(12) United States Patent
Boverman et al.

(10) Patent No.: US 10,874,324 B2
(45) Date of Patent: Dec. 29, 2020

(54) DETECTION OF PHYSIOLOGICAL CHANGES IN IMPEDANCE MONITORING

(71) Applicant: GENERAL ELECTRIC COMPANY, Schenectady, NY (US)

(72) Inventors: Gregory Boverman, Saratoga Spring, NY (US); Tzu-Jen Kao, Watervilet, NY (US); Bruce Courtney Campbell Amm, Clifton Park, NY (US); Jeffrey Michael Ashe, Gloversville, NY (US); David Michael Davenport, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 734 days.

(21) Appl. No.: 14/918,306

(22) Filed: Oct. 20, 2015

(65) Prior Publication Data
US 2017/0105648 A1  Apr. 20, 2017

(51) Int. Cl.
*A61B 5/053* (2006.01)
*A61B 5/00* (2006.01)

(52) U.S. Cl.
CPC ............ *A61B 5/053* (2013.01); *A61B 5/6843* (2013.01); *A61B 5/0536* (2013.01); *A61B 5/746* (2013.01)

(58) Field of Classification Search
CPC .. A61B 5/053–0538; A61B 5/061–063; A61B 5/6843; A61B 5/746
See application file for complete search history.

(56) References Cited

U.S. PATENT DOCUMENTS

| | | | | |
|---|---|---|---|---|
| 4,920,490 A | * | 4/1990 | Isaacson | A61B 5/0536 600/372 |
| 5,272,624 A | * | 12/1993 | Gisser | A61B 5/0536 600/393 |
| 5,807,251 A | * | 9/1998 | Wang | A61B 5/0536 600/407 |
| 6,122,544 A | | 9/2000 | Organ | |
| 7,869,866 B2 | | 1/2011 | Loriga et al. | |
| 8,352,016 B2 | | 1/2013 | Tanaka | |
| 8,779,779 B2 | | 7/2014 | Wang et al. | |
| 8,821,404 B2 | | 9/2014 | Thakur et al. | |
| 2010/0168530 A1 | * | 7/2010 | Chetham | A61B 5/0537 600/301 |
| 2012/0157874 A1 | | 6/2012 | Thakur et al. | |
| 2013/0165755 A1 | | 6/2013 | Thakur et al. | |
| 2015/0366468 A1 | * | 12/2015 | Levy | A61B 5/029 600/526 |

OTHER PUBLICATIONS

Isaacson, David, "Distinguishability of Conductivities by Electric Current Computed Tomography," IEEE Transactions on Medical Imaging, vol. MI-5, No. 2, Jun. 1986 (Year: 1986).*

* cited by examiner

*Primary Examiner* — Matthew Kremer
(74) *Attorney, Agent, or Firm* — McCoy Russell LLP

(57) ABSTRACT

Implementations are disclosed for monitoring a state or change in state of a physiological parameter based on measured impedance data. In certain implementations, no images are reconstructed from the impedance data. In certain implementations, a metric (e.g., distinguishability, likelihood ratios, and so forth) may be computed and compared to reference metrics or thresholds, such as for changes over time or in comparison to a standard to determine the presence or absence of a physiological state of interest or of a change in such state.

17 Claims, 14 Drawing Sheets ured and are used to reconstruct images of the spatial distribution of electrical conductivity and permittivity. With respect to biomedical applications, EIT has been applied to functional neuroimaging, the detection of breast cancer, and to monitoring of respiratory function.

DETECTION OF PHYSIOLOGICAL CHANGES IN IMPEDANCE MONITORING

BACKGROUND

The present specification relates to the use of impedance monitoring, such as electrical impedance monitoring, to detect patient physiological changes without reconstructing an image.

Electrical impedance tomography (EIT) is a biomedical diagnostic imaging technique in which the body is probed noninvasively with generally imperceptible alternating currents applied in patterns to a set of electrodes placed in contact with the skin. In particular, in EIT, patterns of modulated electrical currents or voltages are applied to the surface (or in some cases, to the interior) of an object and the resulting voltages or currents, respectively, are measured and are used to reconstruct images of the spatial distribution of electrical conductivity and permittivity. With respect to biomedical applications, EIT has been applied to functional neuroimaging, the detection of breast cancer, and to monitoring of respiratory function.

Image reconstruction algorithms in conventional approaches are utilized to reconstruct the spatial distribution of the changes in conductivity over time. However, these image reconstruction algorithms are typically quite computationally complex and involve the selection of regularization parameters, a non-trivial challenge.

BRIEF DESCRIPTION

A method for monitoring a physiological state of a patient is provided. In accordance with this method, a pattern of electrical currents (or voltages) is applied to the patient via a set of electrodes positioned on the patient. On one or more of the set of electrodes, a resultant voltage in response to the applied pattern of electrical currents (or resultant current in the case of an applied pattern of voltages) is measured. A change metric is calculated based upon the plurality of measurements. The physiological state or a change in the physiological state of the patient is determined based upon the change metric. In certain embodiments, the applied currents (or voltages) are optimized so as to maximize a metric of change which is of interest, such as the log-likelihood or the maximal distinguishability.

An electrical impedance physiological monitoring system is provided. The system comprises: a plurality of electrodes and one or more electrical channels. Each electrode is in communication with an electrical channel. Each electrical channel comprises: a current source; an excitation source (e.g., a signal generator, such as a sine wave generator); and a response detector. The current source, excitation source and response detector drive operation of the respective electrodes in communication with a given electrical channel. The system further comprises a processor-based monitor configured to operate the excitation source and to receive signals from the response detector in accordance with one or more processor-executable routines. The processor-executable routines, when executed on the processor-based monitor, cause acts to be performed comprising: operating the excitation sources to apply a pattern of electrical currents or voltages to a patient via the plurality of electrodes; operating the response detectors to measure a resultant voltage or current at one or more of the electrodes in response to the applied pattern of electrical currents or voltages; calculating a change metric based upon the plurality of measurements; and determining a physiological state or a change in the physiological state of the patient based upon the change metric.

One or more non-transitory computer-readable media encoding one or more executable routines are provided. The one or more executable routines, when executed by a processor, cause the processor to: apply a pattern of electrical currents or voltages to a patient via a set of electrodes positioned on the patient; on one or more of the set of electrodes, measure a resultant voltage or current in response to the applied pattern of electrical currents or voltages; calculate a change metric based upon the plurality of measurements; and determine the physiological state or a change in the physiological state of the patient based upon the change metric.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
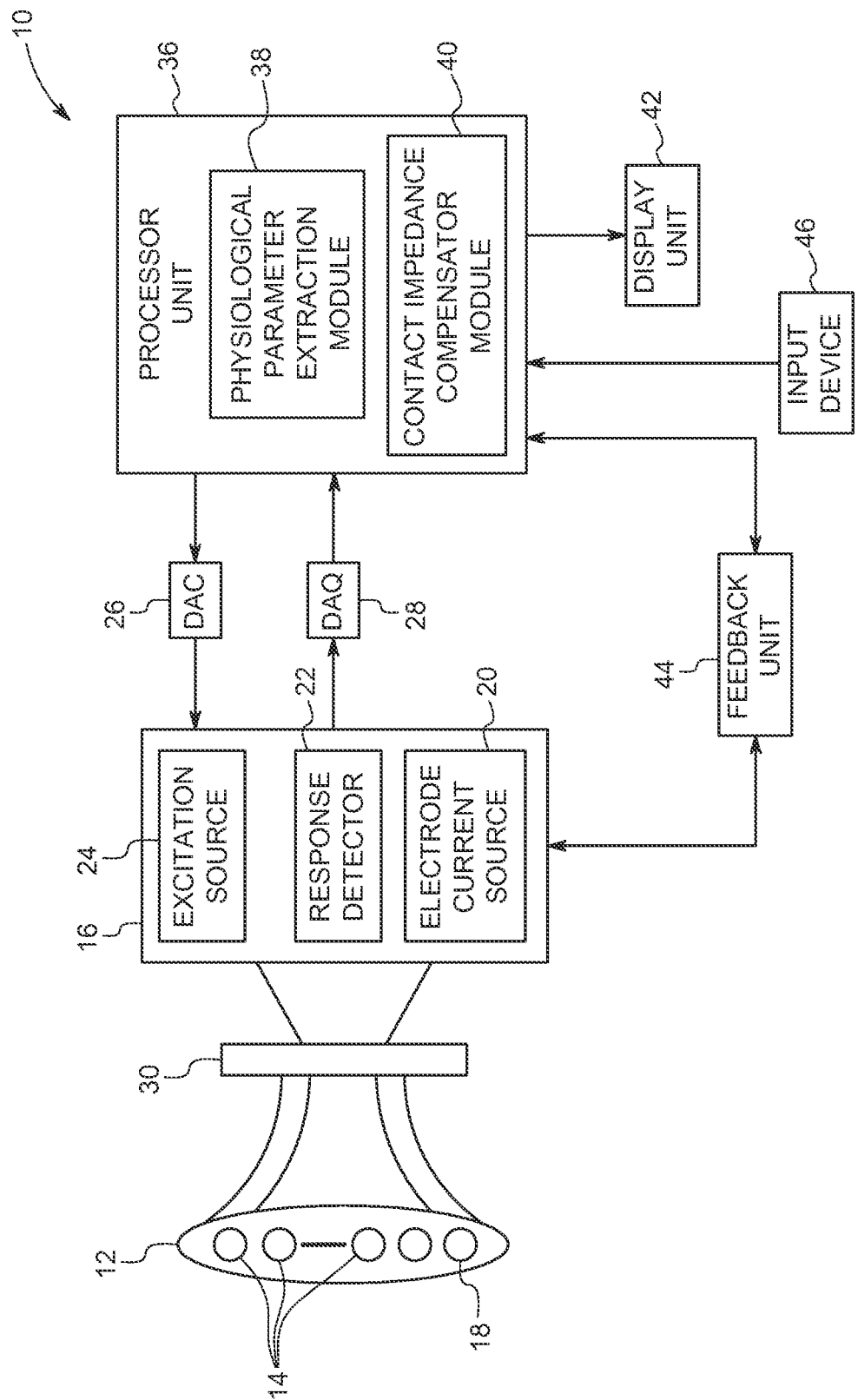
FIG. 1 is a schematic representation of an electrical impedance monitoring system, in accordance with aspects of the present specification.

One or more specific implementations will be described below. In an effort to provide a concise description of these implementations, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various implementations of the present invention, the articles "a," "an," "the," and "said" are intended to mean that there are one or more of the elements and should not be understood as excluding plural of elements or steps, unless such exclusion is explicitly stated. Any numerical examples in the following discussion are intended to be non-limiting, and thus additional numerical values, ranges, and percentages are within the scope of the disclosed implementations. The terms "comprising," "including," and "having", when used, are intended to be inclusive and mean that there may be additional elements other than the listed elements. Unless explicitly stated to the contrary, implementations "comprising" or "having" an element or a plurality of elements having a particular property may include additional such elements not having that property. Furthermore, references to an embodiment or embodiments or to an implementation or implementations herein are not intended to be interpreted as excluding the existence of additional embodiments that also incorporate the recited features or to the combination of features between different described embodiments or implementations.

To the extent that the representative figures illustrate diagrams broken down by particular actions, steps, or functionality, of various implementations, the representative blocks or distinctions drawn or implied are not necessarily indicative of divisions between hardware circuitry. Thus, for example, one or more of the functional or structural blocks (e.g., a processor unit, an electrode current or voltage source, or an excitation source) may be implemented in a single piece of hardware or multiple pieces of hardware and may include software or firmware aspects which are implemented to provide the described functionality. Further, it should be understood that the various implementations are not limited to the arrangements and instrumentalities shown in the drawings.

As discussed herein, changes in electrical conductivity of an internal medium of a subject of interest (e.g., biological material) may be determined by performing measurements on an exterior surface of the subject. The measurements may be performed by disposing a plurality of electrodes on the exterior surface of the biological material. Further, some or all of the plurality of electrodes may be operatively coupled to the biological material.

For the purpose of electrical impedance monitoring, as discussed herein, determined current patterns may be applied to one or more electrodes of a plurality of electrodes at one or more instants in time and resultant voltages may be measured at the one or more electrodes. It may be noted that the measured or resultant voltages are representative of voltage drops along a current pathway which includes both the internal impedance and a boundary contact impedance. Further, as will be appreciated, suitable levels for currents applied to human subjects may be governed by regulations. The currents applied to the human subjects may include intended currents that are generated for a desirable use, unintended currents, currents generated due to a fault in the imaging or monitoring system, or combinations thereof. In one example, the desirable amounts of currents in the current patterns comply with existing standards, such as, but not limited to, IEC 60601-1 standards. It should also be noted that, this scenario may be altered, so as to apply voltages and measure currents, without substantially changing the implementation or procedures discussed herein.

As previously noted, reconstruction of images from electrical impedance measurements may involve the use of image reconstruction algorithms that are computationally complex and that involve the selection of regularization parameters, a non-trivial challenge. As discussed herein, clinically or diagnostically useful information may be determined simply by knowing if a physiological state of a patient of subject changed significantly from a baseline or reference state, without reference to a corresponding image. In such a context, a detected physiological change may be indicative of an alarm condition or of a change in patient state that may justify medical treatment or additional monitoring. Thus, electrical impedance measurements may be used for ongoing or periodic patient monitoring, without reconstruction of tomographic images from the impedance measurement data. By way of example, in certain implementations a physiological state of interest (or a change in a physiological state) may correspond to or result from a change in solid or liquid body tissue composition or spatial distribution. By way of example, such a state or change in state may include changes in the composition and/or spatial distribution of blood, cerebral spinal fluid, calcifications, tumors, and so forth (in contrast to differentiating changes based on the movement of air or gases). For example, for patients being monitored for cerebral bleeding, it may only be necessary to determine if the patient's physiological state (such as a change in the spatial distribution of blood within a monitored region) is significantly different than the initial state in some statistical sense, raising an alarm that would trigger additional measures, such as imaging by an imaging modality having better spatial resolution than EIT.

With this in mind, the present approach employs monitoring of electrical impedance measurements, with or without corresponding reconstruction of EIT images, to directly detect changes in physiological state. Patterns of modulated electrical currents (or voltages) are applied to a set of electrodes placed at specific positions on the body. The specific pattern (spatial and/or temporal) of currents or voltages used may be selected so as to maximize or optimize sensitivity to internal changes. Selection of an optimized pattern can be accomplished due to the medium being probed being a linear system, such that finding the optimal patterns to maximize a given change in measurements can be solved as a constrained optimization problem. These specific patterns typically involve applying currents or voltages and measuring on the same set of electrodes and it has been observed that the contact impedances of the electrodes vary over time. As used herein, the term "contact impedance" and its variations should be understood to correspond to a surface or boundary impedance as used herein and as they are commonly understood. As discussed in greater detail below, vector electrical impedance data may be used for direct classification of patient state, without image reconstruction. In such an approach, changes can be detected either over time (in an ongoing or periodic monitoring application) or across patient populations.

It should be noted that, although described herein primarily with respect to monitoring a current or voltage in a human subject, the electrical impedance monitoring approaches described may be used in other applications, including, but not limited to, defect detection in a manufacturing or fabrication context, geological imaging, and process monitoring. Thus, while the present discussion is useful for non-invasive medical diagnosis (and certain such examples are provided to facilitate explanation), it may also be utilized for imaging the interior of materials other than living tissue. For example, the present approach may be used for geophysical imaging of the earth and oceans and other fields where it may be useful to detect changes in the electrical conductivity and permittivity of the object.

Further, it should be noted that an electrical impedance monitoring system may be any suitable system capable of collecting impedance measurements as described herein, including, but not limited to: an electrical impedance spectroscopy (EIS) system, an electrical impedance tomography (EIT), or an electrical capacitance tomography (ECT) system. By way of example, a suitable system may be one in which electrical impedance measurements are acquired that may be suitable for tomographic image reconstruction but which may also be useful for determinations of changes in physiological states (e.g., changes in solid or liquid body tissue composition or spatial distribution, such as may relate to changes in the composition or spatial distribution of blood, cerebral spinal fluid, calcifications, tumors, and so forth) without reconstruction of a corresponding image. That is, an existing image reconstruction system may instead be repurposed for monitoring or determination of physiological state changes as described herein, while still being able to reconstruct images as needed or desired. Alternatively, a suitable system may be one which is configured to acquire and monitor electrical impedance measurements (in an ongoing or periodic manner) but which is otherwise not configured to reconstruct images. That is, a suitable system may be a dedicated electrical impedance-based monitoring system without imaging functionality. Such a monitoring system may be comparable to an impedance-based tomographic imaging system, but without circuitry dedicated to, or programmed for, image reconstruction.

The systems and methods of the present specification are configured to monitor a medium via electrical impedance measurements acquired using determined current (or voltage) patterns. Additionally, resultant voltages that appear at the electrodes as a result of the applied determined current patterns (or vice versa) may be used to determine electrical properties at a plurality of locations in the subject of interest. In one example, the electrodes may be disposed on a human body for the purpose of monitoring the electrical properties regions inside the body.

With this in mind, and turning to FIG. 1, this figure illustrates an example of an electrical impedance monitoring system 10 in accordance with aspects of the present specification. In the illustrated example, the electrical impedance monitoring system 10 may be used to obtain electrical impedance measurements (e.g., contact impedance measurements) of an object 12 (e.g., a patient or subject). The electrical impedance monitoring system 10 is an electrode-based system that includes a plurality of electrodes 14 disposed at or proximate a surface of the object 12. By way of example, in a healthcare application (e.g., patient monitoring) the plurality of electrodes 14 may be attached to the skin of a patient using a suitable adhesive or as part of a patterned matrix of electrodes 14 pre-positioned on a substrate, such as an adhesive substrate. The electrodes 14 of the plurality of electrodes 14 may be positioned on the surface of the object 12 in different arrangements and may be driven in different configurations.

The electrodes 14 may be formed from any suitable conductive material used to establish a desirable excitation. For example, the electrodes 14 may be formed from one or more metals such as copper, gold, platinum, steel, silver, and alloys thereof. Other suitable materials for the electrodes 14 may include non-metals that are electrically conductive, such as a silicon-based materials used in combination with micro-circuits. In one implementation, where the object 12 is a human body or animal region in which the electrodes are in contact with a skin layer, the electrodes 14 may be formed from silver-silver chloride. Additionally, the electrodes 14 may be formed in different shapes and/or sizes, for example, as rod-shaped, flat plate-shaped or needle-shaped structures.

In operation, the electrodes 14 may be used to deliver an electrical current (or voltage) to the object 12 in a continuous or modulated manner such that excitations may be applied across a temporal frequency range (e.g., 100 Hz to 1 MHz) to the surface of the object 12 to generate an electromagnetic field within the object 12. The resulting voltages (real, imaginary or complex) on the electrodes 14 (or currents in the case of applied voltages) may be measured to determine an electrical impedance (e.g. electrical conductivity or permittivity distribution), which is used to separate or distinguish different physiological parameters. As discussed herein, contact impedances may exist at an interface between an electrode and a material that the electrode is physically in contact with. In one example, in case of the electrode skin contact, the contact impedance exists at the electrode-skin interface and may be referred to as electrode-skin contact impedance.

The currents driving one or more electrodes 14 may be at different frequencies or at the same or substantially similar frequencies. In certain of these examples, the currents having the same or substantially similar frequency may have different phases (e.g., 0 degrees, 90 degrees, 180 degrees and 270 degrees). It should be noted that some of the electrodes 14 may have no current applied thereto. Such electrodes 14 may be used only for voltage measurements in these instances.

Moreover, the plurality of electrodes 14 may include a reference electrode 18. The reference electrode 18 is configured to receive currents from all the electrodes 14. Accordingly, a reference current at the reference electrode 18 is a cumulative sum of the currents applied to the various electrodes 14. Also, the reference electrode 18 is attached to the object to provide a reference potential and may not be intended to source or sink the current during normal operation. In one example of a suitable system, the plurality of electrodes 14 may have thirty-two electrodes to which currents are applied, although other suitable numbers of electrodes may be employed in other implementations. Although not illustrated, in some instances, two or more reference electrodes 18 may be employed in the electrical impedance monitoring system 10.

Additionally, in practice the electrodes 14 may be operatively coupled to a plurality of electrical channels 16. Although the illustrated example shows only one electrical channel 16, the electrical impedance monitoring system 10 may employ a plurality of electrical channels 16. Each electrical channel 16 may include an electrode current source 20, an excitation source 24 (e.g., a signal generator), and a response detector 22.

Further, each electrode 14 of the plurality of electrodes 14 may be operatively coupled to a corresponding electrical channel 16 of the plurality of electrical channels 16. Each electrical channel 16 of the plurality of electrical channels 16 may be configured to provide a specified amount of current (or voltage) to the corresponding electrode 14 of the plurality of electrodes 14. Further, the specified amount of current may be below a threshold value of the applied current. Further, the electrical channels 16 may be configured to be de-energized or operatively disconnected from the plurality of electrodes 14. In one example, the plurality of channels 16 may be disconnected from their respective electrodes 14 using an electrically controlled switch (e.g., an output relay) configured to de-energize the corresponding channel 16 when an output current to the subject is higher than an established threshold value.

In addition to the electrode current source 20, each electrical channel 16 may include an excitation driver or excitation source 24 and a response detector 22 that are coupled to the electrodes 14. Also, the excitation source 24 and the response detector 22 are each connected to a processor-based monitor unit 36 (e.g., a computing device or dedicated monitor). In some instances the excitation source 24 and the response detector 22 are physically separate devices. However in other instances the excitation source 24 and the response detector 22 can be physically integrated as one element. The processor-based monitor unit 36 may transmit instructions to the excitation source 24 through a digital-to-analog converter (DAC) element 26 and receives data from the response detector 22 through a data-acquisition (DAQ) element 28. It should be noted that one or more excitation sources 24 may be provided such that one excitation source 24 is provided per electrode 14, for a subset of electrodes 14 or for all the plurality of electrodes 14.

The excitation source 24 may be a signal generator circuit (e.g., a signal generation ASIC) that produces a waveform signal (e.g., a sine wave generator). Though a discrete and separate excitation source is shown and described here for clarity, it should also be appreciated that signal generation may instead be performed by executing a suitable generation routine using a processor of the processor-based monitor 36, in which case a discrete and separate excitation source 24 may be absent. Each of the excitation sources, whether discrete circuits or implemented using a processor generate signals having a certain, discrete strength, determined by spatial and temporal factors, as discussed in greater detail below with respect to pattern generation.

In the depicted example, a multi-wire measurement configuration is provided that uses different electrodes 14 for excitation from the excitation source 24 and measurement by the response detector 22. In some implementations, two or more electrical channels 16 may share the same excitation source 24 and/or the response detector 22. The electrical channels 16 may be operatively coupled to their respective electrodes 14 using an interface 30. In particular, the connection between the electrodes 14 and one or both of the excitation source 24 and the response detector 22 may be provided via the interface 30. In some instances the excitation source 24 applies an excitation current to one or more of the electrodes 14 with a voltage response measured by one or more electrodes 14 though, as noted above, this arrangement may be reversed, with a voltage applied and a current measured.

With the preceding in mind, and by way of example, a suitable system 10 may have the capability of applying currents and measuring voltages on thirty-two channels 16 simultaneously. Such a system 10 may be capable of collecting thirty-one patterns applied to thirty-two electrodes 14, giving a total of 992 complex measurements, at a frame rate of at least 20 Hz.

With further regard to the system 10, a physiological parameter extractor 38 may be implemented within the processor-based monitor unit 36. Further, the physiological parameter extractor 38 may be implemented within the hardware (e.g., as an application specific integrated circuit (ASIC)) or a combination of the software and hardware (e.g., as a programmed or programmable circuit). In addition to the physiological parameter extractor 38, the processor-based monitor unit 36 may also include a contact impedance compensator 40, which may also be implemented within the hardware (e.g., as an ASIC) or a combination of the software and hardware (e.g., as a programmed or programmable circuit). The contact impedance compensator 40 may be configured to provide compensation at least in part for a change in the contact impedance of one or more electrodes 14. The contact impedance compensator 40 may include software and/or hardware aspects configured or programmed to execute steps to compensate for the change in contact impedances. Further, the contact impedance compensator 40 may include computer executable instructions in the form of routines, programs, objects, components, data structures, procedures, modules, functions, and the like that perform determined process steps, such as by execution of such routines or programs by a processor or processing components of the processor-based monitor unit 36. Moreover, the contact impedance compensator 40 may include a sequence of operations that may be implemented in hardware, software, or combinations thereof.

Additionally, the system 10 may further include a display unit 42 configured to display the data processed by the processor-based monitor unit 36. The display unit 42 may include one or more monitors that display patient information, such as indications of the presence or absence in changes in physiological states of interest or the patient. The display unit 42 may automatically display data stored in the memory or currently being acquired, i.e., monitored. This stored data may also be displayed with a graphical representation, such as a chart or graph showing changes in the monitored data over time.

The system 10 may also include a feedback unit 44. The feedback unit 44 may be operatively coupled to the processor-based monitor unit 36. Further, the feedback unit 44 may be operatively coupled to one or more electrical channels 16. The feedback unit 44 may be configured to provide feedback to the processor unit 36 regarding the resultant voltages at the electrodes 14. The feedback unit 44 may be configured to communicate with the processor-based monitor unit 36, electrical channel 16, or both. In particular, the feedback unit 44 may be configured to instruct one or both of the processor-based monitor unit 36 or the electrical channels 16 to exclude the contribution of the electrodes that are not properly coupled to the subject of interest. By way of example, in instances where one or more electrodes 14 are not coupled properly to the subject of interest, the feedback unit 44 may be configured to provide feedback to the processor unit 36 to reject the values, such as the resultant voltages and the contact impedances associated with that particular electrode 14. Upon receiving instructions from the feedback unit 44, the processor unit 36 may be configured to provide (or not) a determined current pattern to the corresponding electrical channel 16.

Further, the system 10 may include one or more input devices 46 that are communicatively coupled to the processor unit 36. The input devices 46, for example, may include a keyboard, a mouse, a trackball, a joystick, a touch-activated screen, a light wand, a control panel, and/or an audio input device such as a microphone associated with corresponding speech recognition circuitry. The input devices 46 may also allow a user, such as a medical practitioner to input information/instructions, such as, but not limited to, determined or pre-configured current patterns.

It should be noted that the system 10 may be implemented, for example, as one of various types of soft-field tomography systems, such as the EIS, EIT, or ECT and related modalities. Alternatively, the system 10 may be implemented as a dedicated electrical impedance monitoring systems having no tomography or imaging capabilities but otherwise providing ongoing or periodic electrical impedance monitoring and monitoring of changes in physiological states of interest.

Furthermore, data acquisition and processing steps, as discussed in greater detail below, may be performed by the system 10 and may be implemented using suitable code, firmware and/or ASICs on a processor-based system, such as the monitor 36. It should also be noted that different implementations may perform some or all of the steps described herein in different orders or substantially concurrently, that is, in parallel. Furthermore, the functions may be implemented in a variety of programming languages, including but not limited to C++ or Java. Such code may be stored or adapted for storage on one or more tangible, machine readable media, such as on data repository chips, local or remote hard disks, optical disks or media (that is, CDs or DVDs or optical or scannable code), memory, or other media, which may be accessed by a processor-based system to execute the stored code.

As discussed herein, a system 10, such as that discussed above, may be used to monitor and analyze measured patient impedance data (e.g., vector electrical impedance data) for direct classification of patient state, with or without image reconstruction, thereby allowing detection of physiological changes over time or across patient populations. In certain aspects, compensation for electrode contact impedance changes may be performed (i.e., these changes may be removed or compensated in the measured voltages. After compensation for these electrode contact impedance changes, a change metric (e.g., distinguishability, likelihood ratios, and so forth) can be computed of the difference between a given measured data vector and a second data vector to ascertain whether a reportable or alarm event has occurred. These data vectors may come from two different individuals (such as for diagnostic or comparative purposes) or from the same individual at a second point in time (such as for diagnostic or change detection purposes). By way of example, after compensating for electrode contact impedance variations, if necessary, the metric may be computed of the difference between the two data frames and, using statistical testing methods, a determination may be made as to whether there has been a significant change. If there has been a significant change, an alarm condition may be indicated (e.g., visually and/or audibly) or a physiological change otherwise reported, signaling personnel to take additional action, such as acquiring further medical imaging or applying an medically indicated treatment, as indicated.

Alternatively, the difference between two data vectors may be discerned for periodic or semi-periodic physiological processes such as respiration or cardiac events. In such an implementation, the difference may be used to optimally or maximally distinguish between states, levels, or degrees (e.g., end-points, start-points, mid-points) of these periodic or semi-periodic processes, such as distinguishing between full inspiration and end-expiration in respiration.

Figure 2:
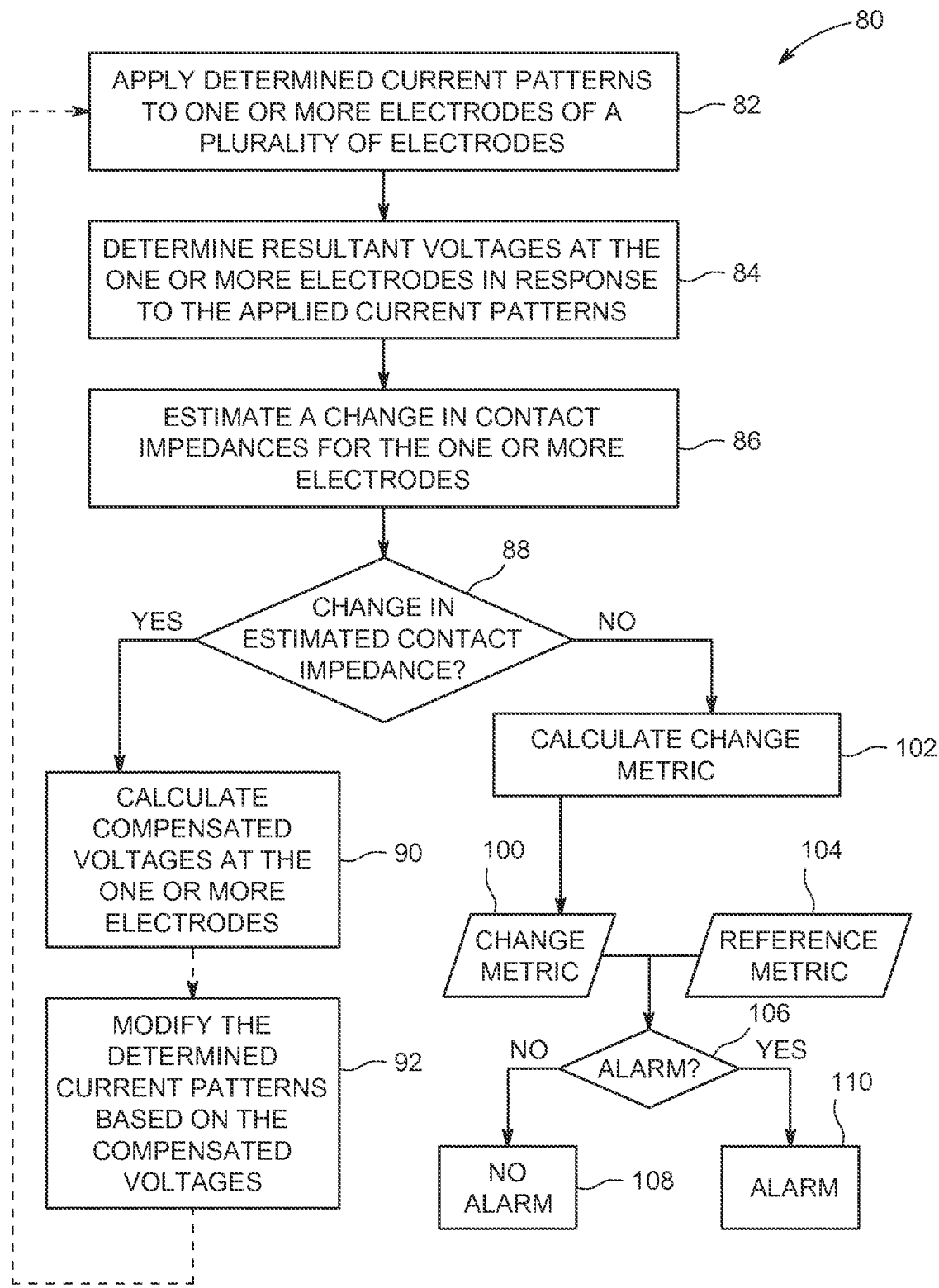
FIG. 2 is a block diagram of an example method for impedance imaging of a subject of interest using a plurality of electrodes, in accordance with aspects of the present specification.

By way of example and turning to FIG. 2, a process flow 80 of one example of electrical impedance monitoring of a subject of interest using a plurality of electrodes is depicted. The method 80 provides for compensating for a change in contact impedances of one or more electrodes of the plurality of electrodes. Thus, in some (but not all) instances the one or more metrics (e.g., distinguishability, likelihood ratios, and so forth), as discussed above, may be compensated to account for the change in the contact impedances. The metrics may be processed and/or generated in an ongoing or periodic manner to provide an indication to a change in a physiological state of a patient.

The method 80 may be iterative in nature, such as in an ongoing monitoring application. In such scenarios, the estimated change in the contact impedances may be used to modify the determined current patterns for one or more electrodes, as shown by dashed lines in FIG. 2. The modified (or optimized) current patterns may be then applied to the one or more electrodes, and the change in the contact impedances may be measured accordingly. Though the application of a current and the measurement of a voltage is shown and discussed with respect to FIG. 2 by way of example, it should be recognized that the mathematically equivalent case of applying voltages and measuring currents is also implicitly covered and disclosed.

At block 82, determined current patterns may be applied to one or more electrodes of the plurality of electrodes. In certain instances, the determined current patterns may be applied as pairwise current patterns. For example, determined current patterns may be applied for each pair of electrodes of the plurality of electrodes.

In some circumstances, the determined current patterns may be configured to maximize the ability of the plurality of electrodes to detect changes in an internal medium given a constrained input power, where the constrained input power may be defined by regulatory or other concerns. Further, the determined current patterns may be optimal current patterns that are configured to maximize percent distinguishability, log-likelihood, and so forth. It may be noted that distinguishability may vary with respect to time due to physiological changes and/or the electrode drift. Moreover, when distinguishability due to the electrode drift is relatively large, physiological changes that possess a lower distinguishability may not be readily observable without compensation and/or optimization, as discussed herein. Thus, it is desirable to compensate for the electrode drift so that the system remains suitably sensitive to observe the desirable physiological changes.

With respect to the determination of a current (or voltage) pattern to be applied at step 82, it should be appreciated that a pattern (e.g., an optimal pattern) may be determined based on (or estimated) using a priori knowledge (e.g., the geometry of the body, internal conductivity, known separation distances between electrodes, and so forth). Alternatively, in view of the known linear response between applied current and measured voltage (and vice versa), this linearity may be used to adaptively determine an optimal pattern empirically, i.e., by applying an initial, arbitrary current or voltage pattern, comparing the measured values to the theoretical or expected values, and adjusting the initial pattern in view of this comparison so as to generate an optimal pattern.

At block 84, resultant voltages in response to the applied determined current patterns (or vice versa) may be determined for the one or more electrodes. Further, the resultant voltages may be determined for each individual electrode of the one or more electrodes. By way of example, a determined current pattern may be applied to an electrode and a resultant voltage may be determined for the same electrode. Whereas, in other instances pairwise current patterns may be applied. In these contexts the resultant voltages may be determined for one or more pairs of the electrodes. Additionally, where optimal current patterns are applied to the plurality of electrodes, the resultant voltages for each individual electrode or the one or more pairs of electrodes may be determined using mathematical decomposition.

Further, the resultant voltages may be determined at two or more instants in time. In one example, the resultant voltages may be determined for a given electrode at the beginning of a monitoring interval or period (t=0) and after passage of a determined period of time (t=T). Similarly, the resultant voltages may be determined for the pairs of electrodes at two or more instants in time.

At block 86, a change in contact impedances may be estimated for the one or more electrodes of the plurality of electrodes. The change in the contact impedances may be estimated for each pair of electrodes of the plurality of electrodes. Alternatively, the change in the contact impedances may be estimated for each electrode of the one or more electrodes for two or more instants in time. By way of example, the change in the contact impedances may be estimated for each pair of electrodes of the one or more electrodes for two or more instants in time.

Estimating the change in the contact impedances may include estimating individual contact impedances for a given electrode at two or more instants in time, and determining the difference between the contact impedances at the two or more instants in time. Alternatively, estimating the change in the contact impedances may include estimating individual contact impedances of a pair of electrodes, and determining the change in the contact impedance for the pair of electrodes based on the estimated individual contact impedances. The contact impedances may be estimated using predefined fitting models. For example, the contact impedances may be estimated using a least-square fit model or other suitable fitting or optimization model.

The contact impedances may have complex values that have real and imaginary parts. In some instances, the contact impedances may be estimated using a resistance-based model. Further, in the case of the resistance model, it may be assumed that the contact impedances may have real and positive parts. Alternatively, in other implementations, a series resistance-capacitor model may be used to estimate the complex impedances. In the case of the resistance-capacitance model, it may be assumed that the values of the contact impedances may be represented as complex values that have a positive real part and a negative imaginary part. Moreover, the contact impedances may also be estimated using a parallel resistance-capacitor model. In such circumstances, the real part may be constrained to be positive and the imaginary part may be constraint to be negative.

Depending on the predefined model that is selected to estimate the contact impedances, further constraints may be provided based on one or more predefined constraints. By way of example, minimum and maximum values of resistance and capacitance may be assumed when using the series or parallel resistance-capacitor models.

Although discussed with respect to resistances, the change in contact impedances may be estimated using a change in one or more other suitable properties over time. Non-limiting examples of such properties may include electrical conductivity, permittivity, and frequencies of currents of the current patterns with respect to time.

The estimated contact impedances may be filtered. For example, the estimated contact impedances may be filtered to exclude desired signal changes in the impedances of the internal medium. By way of example, the estimated contact impedances may be filtered to remove changes in the contact impedance that are contributed by known or estimated physiological phenomenon. Thus, the changes in the contact impedances due to physiological phenomenon, such as, but not limited to, heart or breathing signals may be filtered out from the estimated contact impedances. Further, in another example, filtering may be performed to remove expected temporal or spectral physiological signals from the estimated changes in the contact impedances. Filtering may also be performed to exclude physiological signals by fitting the estimated change in the contact impedances to an exponential function based on electrode drift time constants.

Additionally or alternatively, the estimated contact impedances may be filtered to retain desired changes in the contact impedances due to the electrode-skin interface. By way of example, the estimated contact impedances may be filtered to retain contribution in the change of the contact impedance due to drift in the electrode. Further, in one example, filtering may be performed to include expected changes in temporal or spectral contact impedances while estimating the changes in the contact impedances. In some instances, filtering may include fitting contact impedance change vs. time to a desirable model. Non-limiting examples of the desirable model may include an exponential function, a linear function, a quadratic function, a $3^{rd}$ order function, a function having an order higher than the $3^{rd}$ order, or combinations thereof.

A plurality (i.e., two or more) of current frequencies may be used in the determined current patterns to verify or to provide additional data to further enhance the estimation of the change in the contact impedances. In estimating the change in the contact impedance it may be assumed that the internal medium of the subject of interest remains constant.

At block 88, it may be determined whether there has been a change in the contact impedance for each electrode or each pair of electrodes of the one or more electrodes. By way of example, if the estimated value of the change in the contact impedance (block 86) for an electrode is zero, it signifies that there has been no change in the contact impedance. Further, if the estimated value of the change in the contact impedance for a given electrode is a non-zero value, it suggests that the contact impedance for that particular electrode or pair of electrodes may have changed.

At block 90, if there is a change in the contact impedances of the one or more electrodes of the plurality of electrodes, compensated voltages for each individual electrode or each pair of electrodes may be calculated based on the estimated change in the contact impedances. The compensated voltages may be calculated by subtracting a portion of the voltage from the resultant voltage, where the portion of the voltage corresponds to the change in the contact impedance or by other suitable compensation or negation approaches.

In instances where there is no change in the contact impedance of any of the electrodes or the pair of electrodes, the change metric 100 (discussed in greater detail below) may be calculated (block 102) without modifying the values of the resultant voltages to compensate for the change in the contact impedances. Accordingly, as indicated by block 102, the change metric 100 may be calculated based on the determined current patterns, the resultant voltages, and the compensated voltages.

Optionally, at block 92, the determined current patterns may be modified based on the estimated changes in the contact impedances. The modified current patterns may then be applied, and corresponding resultant voltages, changes in the contact impedances, and compensated voltages may be measured for the modified current patterns. In this manner, the method for compensating for the change in the contact impedances may be performed in an iterative fashion. Accordingly, after determining the modified current patterns, steps represented in blocks 82, 84, 86, 88, 90, and optionally step 92 may be repeated one or more number of times, such as until a specified completion criteria is satisfied. The number of iterations may be decided by a user operating the monitoring system or by preconfigured coding within the system 10. For example, the number of iterations may be decided based on one or more parameters, such as, but not limited to, a difference in values of the resultant voltages and the compensated voltages, or distinguishability criteria associated with the change metric 100.

In certain implementations, the change metric 100 may be compared (block 106) to a reference metric 104 (such as a previous metric calculated for a given patient, for a given population, such as metric determined to be indicative of a condition of interest exhibited by the population). Based on the comparison, it may be determined that no reporting or alarm condition 108 exists or that a reporting or alarm condition 110 is present and that a notification should be provided to a caregiver.

By way of example, data from patients with hemorrhagic strokes versus those with ischemic strokes may be clustered (e.g., used to generate reference metrics 104 and used to classify a given patient by means of his or her distance to each of the clusters, i.e., by comparison of a monitored change metric 100 with the respective stroke reference metrics. In such an approach, the goal is to classify whether a given condition is present (i.e. that of a hemorrhagic stroke), producing a binary decision at the comparison step. Based on this comparison, a determination is only made as to the presence or absence of the referenced condition, and the characterization and localization of the changes in question (e.g., the location and/or severity of the stroke) may be left to other techniques, such as magnetic resonance imaging or computed tomography, for subsequent determination.

Alternatively, as noted herein, rather than classification, the present approach may be used to characterize periodic or semi-periodic physiological processes, such as respiration or heartbeat. For example, the distinguishability metric for respiration is roughly periodic. Thus, using distinguishability, a better estimate of the respiration rate or the heart rate may be computed than would be possible using a single impedance measurement.

With the preceding comments in mind, the following examples and discussion are intended to provide greater detail and/or examples of useful implementations. In particular, the present approach pertains to various mathematical and algorithmic approaches to detecting changes in impedance measurements. There are a variety of application areas where such algorithms could be of use. For example, one possible application is for monitoring patients for cerebral, or other internal, bleeding, where a single metric could be generated using the approach disclosed herein and used for determining whether a significant amount of bleeding has occurred. One possible such metric could be the maximum distinguishability, after compensation for electrode contact impedance changes, as discussed above. Another possible application could be monitoring of pediatric patients with hydrocephalus to determine whether cerebrospinal fluid is accumulating over time.

With respect these applications, the detection of small bleeds in the brain using electrical impedance measurements is now discussed. In the discussed study, electrical impedance measurements are shown as suitable to detect small bleeds within the head (i.e., not on the periphery) having a volume of several milliliters. As noted above, one aspect of the discussed study is the compensation of changes in voltage that may occur when the electrodes are in contact with biological media, specifically either human subjects or with vegetable matter proxies which seem to exhibit the same drift phenomenon.

As discussed in this example, these changes in voltages can be modeled by assuming that each electrode is attached to the body via a discrete complex impedance whose value is time-varying. An approach describing how this discrete component value can be estimated and largely compensated for is provided. In a simulation study, it is demonstrated that it is possible to detect a small bleed in the center of the head even in the case of large changes in electrode contact impedances, which can be treated as nuisance parameters.

As discussed herein, one can optimize sensitivity in electrical impedance measurements by applying currents and measuring potentials on some or all electrodes (i.e., multiple applied electrodes), in particular by applying the specific patterns that maximize the "distinguishability" of internal changes in admittivity. However, such an approach may introduce challenges in that measuring the potential on current-carrying electrodes maximizes our sensitivity to changes in skin-electrode contact impedance, which can be confounding. As disused herein, a number of methods for estimating and removing these changes from the measurements may be employed, allowing for the practical implementation of multiple excitation electrical impedance measurements to detect slowly-varying physiological changes, such as the development of a slow bleed.

One problem to be addressed, which is discussed herein, is whether electrical impedance measurements acquired with optimal currents maximizing the distinguishability of conductivity changes deep within the brain can detect such changes even in the presence of large variations at the electrode-skin interface. With this in mind, a simplified discrete model estimating variations in electrode-skin contact impedance as a function of time is described. Given that these variations can be estimated, a compensated data set can be generated based on the estimates, where the compensated data set is the set of measurements that would be have been obtained had the superficial variations, which are generally not of interest, not taken place. In a normal human subject experiment, this simplified model gives results that are qualitatively similar to, but not quantitatively identical to, those obtained using a linearization of the complete electrode model (CEM) and its ability to explain changes occurring at the interface of the electrodes and the body is comparable to that of the CEM. In the context of the described study, both models were able to explain not less than 96% of the variance in the measurements asymptotically.

In the context of this study, the feasibility of detecting a relatively small bleed in the brain given that relatively large changes in electrode-skin contact impedances are simultaneously occurring is also shown. In this study, using a realistic finite-element mesh generated from a segmented CT scan, and assuming literature-derived impedance properties for the various tissue types, a simulated bleed of known volume was modeled at a known location. The actual currents typically used in a suitable electrical impedance monitoring system were simulated along with a number of randomly generated realizations of independent, identically distributed (i.i.d.) Gaussian noise to the real and imaginary parts of the measured voltages, with variances derived from experiments with known, non-time-varying loads such as discrete resistors, capacitors, and R-C circuits. Given knowledge of electrical properties, brain geometry, applied currents, and noise variances, a detailed Monte Carlo simulation was generated of the detection performance of the instrument with a bleed of known volume and position. A simulation was also generated where, in addition to random noise, there was systematic variation in electrode-skin contact impedances with statistical properties derived from a normal human subject study. In this simulation, the effect of electrode-skin contact impedance variations were suitably compensated and, for the case of a small bleed in the center of the head, detection performance was shown to be only slightly degraded in the case of systematic contact impedance variations in addition to random measurement noise.

Mathematical Modeling—In electrical impedance physiological monitoring, it may be assumed that the potential in the body is governed by the following partial differential equation, which is derived from Maxwell's equations:

$$\nabla \cdot \gamma \nabla u(p) = 0, \text{ for } p \text{ in } \Omega \quad (1)$$

where u(p) is the scalar potential as a function of position, p, γ is the conductivity distribution, Ω is the spatial extent of the medium being probed, ∇· is the divergence operator and ∇ is the gradient operator. This equation has been found to be empirically valid at low temporal frequencies, however modeling based on the direct application of Maxwell's equations may be necessary at higher frequencies.

With the preceding in mind, in a differential measurement or imaging context, it may be effective to approximate the change in the surface impedance as the change in a discrete component in series with the object being measured, as opposed to implementing the full complete electrode model, which would necessitate the calculation of various surface and volume integrals in the bases of the finite elements. The Jacobian with respect to changes in this discrete component value may be computed as follows:

$$J_{i,k,j} = \begin{cases} I_{j,k} & \text{if } i = j \\ 0 & \text{if } i \neq j \end{cases} \quad (2)$$

Here $J_{i,k,j}$ is the term of the Jacobian matrix for electrode i and current pattern k with respect to a change in the discrete impedance at the interface of electrode j and the body, where the current on electrode i of current pattern k is $I_{i,k}$.

Based on this, the following model for differential imaging and/or measurements may be represented:

$$y(t) = y(0) + J_z \delta z(t) + J_\gamma \delta y(t) + c(t) y(0) \quad (3)$$

where y(t) is the measurement vector at time t, y=(0) is the measurement vector at the initial time, δz(t) is the change in contact impedances at time t, δγ(t) is the vector of changes in internal admittivities at time t and c(t) is a global change in the admittivity of the entire medium. The Jacobian matrix of the measured voltages with respect to a change in electrode contact impedances is $J_z$ and the Jacobian matrix of the measured voltages with respect to a change in medium admittivities is $J_\gamma$. These quantities can be estimated separately or a coordinate descent procedure may be used to estimate one quantity based on the others. The estimation of the contact impedances δz(t) is typically a well-posed problem, while the estimation of δγ(t) typically is very ill-posed and requires regularization. As noted, an advantage of the discrete model is that estimation of the global conductivity and of the absolute contact impedances is not necessary for computation of the Jacobian matrix.

Data Difference and Distinguishability—In order to assess the raw difference between two data frames, without image reconstruction, the concept of "power distinguishability" is employed with respect to the examples discussed herein. In view of a noise model, such as assuming that the voltage noise level is not affected by the applied current, it is useful to also consider a voltage distinguishability metric. With respect to the present study and examples, three metrics of distinguishability are defined between a frame at time T and a reference frame at time $t_0$: maximum distinguishability, minimum distinguishability, and total (or mean) distinguishability, which are defined as follows:

$$D_{max} = \max_k \frac{\sum_{j=1}^{N} |I_{j,k} V_{j,k}(t_T) - I_{j,k} V_{j,k}(t_0)|}{\sum_{j=1}^{N} |I_{j,k} V_{j,k}(t_0)|} \quad (4)$$

$$D_{min} = \min_k \frac{\sum_{j=1}^{N} |I_{j,k} V_{j,k}(t_T) - I_{j,k} V_{j,k}(t_0)|}{\sum_{j=1}^{N} |I_{j,k} V_{j,k}(t_0)|} \quad (5)$$

$$D_{total} = \frac{\sum_{k=1}^{K} \sum_{j=1}^{N} |I_{j,k} V_{j,k}(t_T) - I_{j,k} V_{j,k}(t_0)|}{\sum_{k=1}^{K} \sum_{j=1}^{N} |I_{j,k} V_{j,k}(t_0)|} \quad (6)$$

where $I_{j,k}$ is the current on electrode j for current pattern k and $V_{j,k}(t)$ is the corresponding voltage on electrode j for this current pattern at time t. At each time instant, the changes in the electrode contact impedances δz(t) and the global scaling factor for the resistivity, c(t) are estimated by solving equation (3), such as by using the linear least squares method. The "compensated" voltages, which are the voltages that would have been measured had the contact impedance remained constant, are then computed as:

$$y_{comp}(t) = y(t) - J_z \delta z_{est}(t) - c_{est}(t) y(0) \quad (7)$$

where $\delta z_{est}(t)$ is the vector of estimated complex contact impedances at time t and $c_{est}(t)$ is the estimated scaling factor for the global impedance at time t. A constraint that the voltages on all electrodes sum to zero for each pattern at each point in time is applied after compensation for changes of measured voltages due to changes in electrode-body contact impedances in one implementation.

Instrumentation Noise—With respect to the presently described study, in order to assess the noise floor of the instrument in question, an experiment was conducted to measure the voltages generated when driving currents of varying levels through known purely resistive, purely capacitive, and parallel R-C circuit loads. In general it was observed that there was a systematic drift in the measured voltages that was proportional to the applied current. This systematic component could be eliminated by fitting a third order polynomial in time for the real and imaginary parts of the measured signals. The residual voltage noise was then computed, confirming that it was independent of the applied current amplitude. It was observed that the magnitude of the residual differed depending on the load, which may be due to the temporal filtering nature of the capacitive loads. However, for all of the loads, a maximum residual standard deviation of approximately 5 µV was observed.

Study Configuration and Analysis—With respect to the present approaches, studies of normal human subjects were conducted to ascertain what distinguishability differences might be observed in the raw data under typical experimental conditions. An EasyCap (EASYCAP GmbH, Herrsching, Germany) electrode mesh with Ag—Cl electrodes was utilized and Elefix electrode paste (Nihon Kohden, Tokyo, Japan) was spread at the electrode-scalp interface to minimize the contact impedance at the interface. One goal was to reduce the real part of the impedance between each electrode and an electrode-patch ground placed at the shoulder to a level below 3 k Ohms at 10 kHz, and it was observed that for most subjects, including those with thick hair, this was possible with repeated applications of electrode gel.

Figure 3:
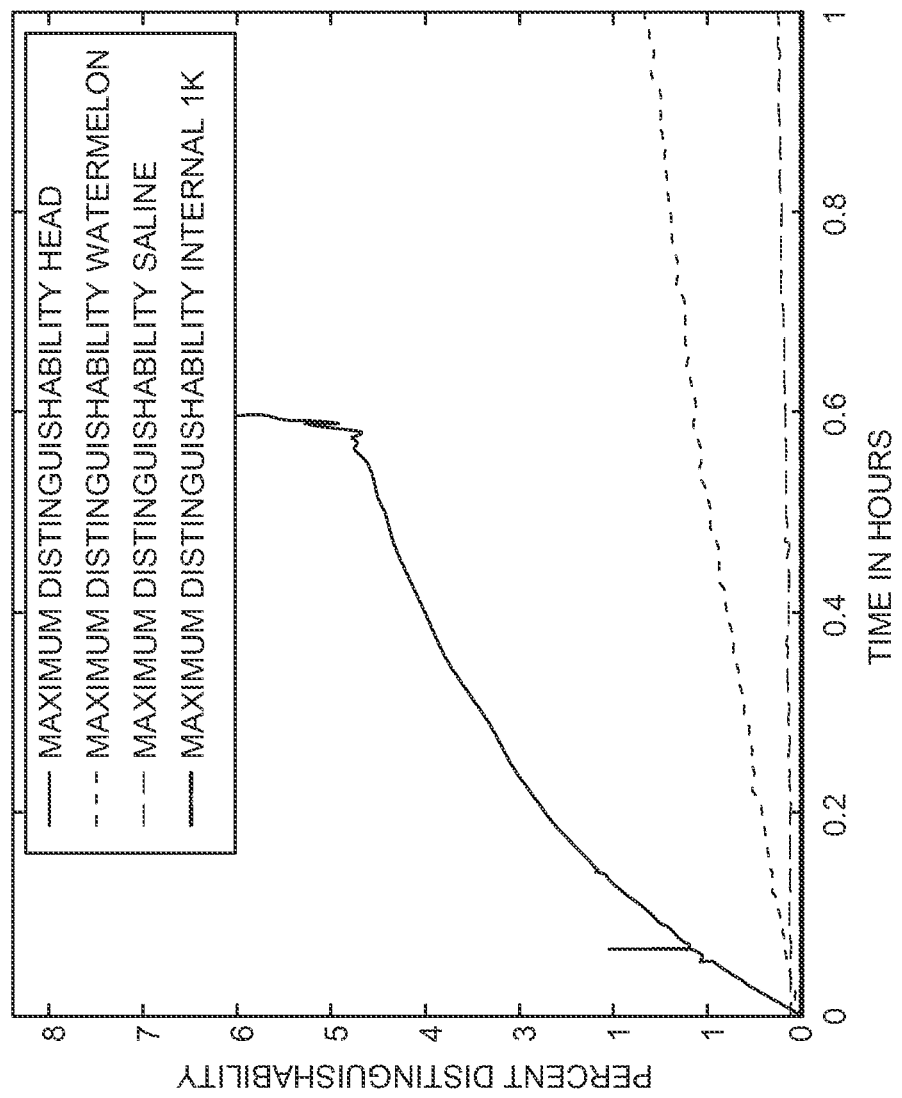
FIG. 3 depicts distinguishability over time for a variety of objects, in accordance with aspects of the present specification.

One aspect of the study measured the voltages from a normal human subject applying optimal patterns to maximize distinguishability (measuring the voltage on current-carrying electrodes) for approximately 45 minutes and also measured the voltages for various phantoms, such as a watermelon with attached electrode cap, a saline-filled tank, and the internal resistors used to test the system. These results are shown in FIG. 3, where it can be observed that there were significant distinguishability differences for the human subject and watermelon, but relatively small differences for the saline tank and the internal resistors. These differences are believed to be due mostly to electrochemical processes at the boundary contact interface and the simplified algorithm discussed above was able to estimate these differences and largely compensate for them.

Figure 4:
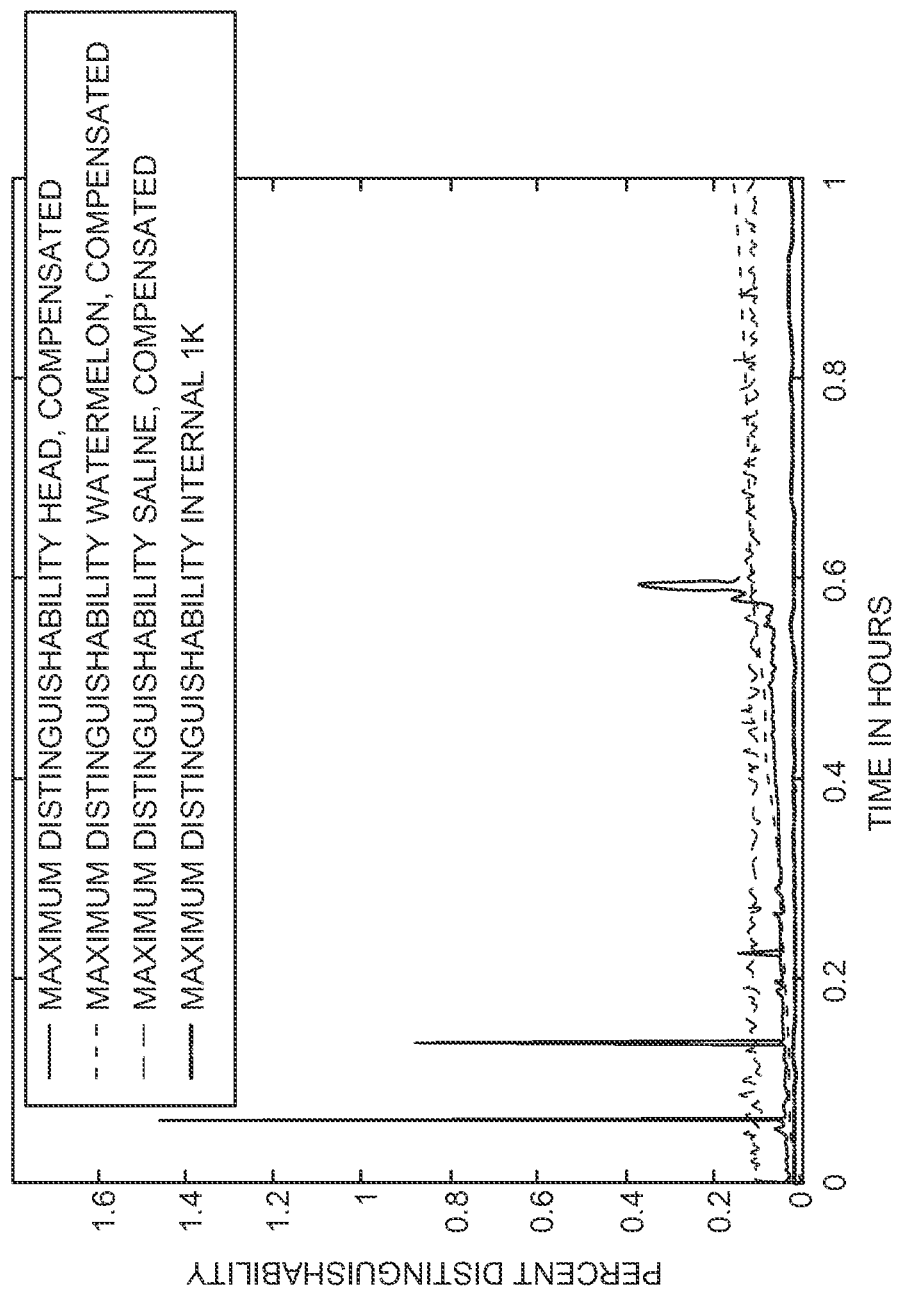
FIG. 4 depicts distinguishability over time for a variety of objects using compensated voltages, in accordance with aspects of the present specification.

The distinguishability changes after compensation are shown in FIG. 4. The majority of the distinguishability of the human subject data can be attributed to contact impedance changes at the interface between the electrodes and the skin. It is also believed to be a significant observation that the distinguishability changes over time for electrodes in contact with a human subject or with vegetable matter are much greater than those for stainless steel electrodes embedded in a saline-filled tank and for measurements of internal discrete resistor components. One possibility for explaining these differences is that the AgCl electrodes used in the human and watermelon experiments were used in conjunction with an electrolyte gel whose chloride concentration differed significantly from that of the body and therefore there may have been diffusion of chloride ions into the body over time. Additionally, the effective impedance of the skin may change over time due to changes in moisture content (i.e., perspiration).

Figure 5:
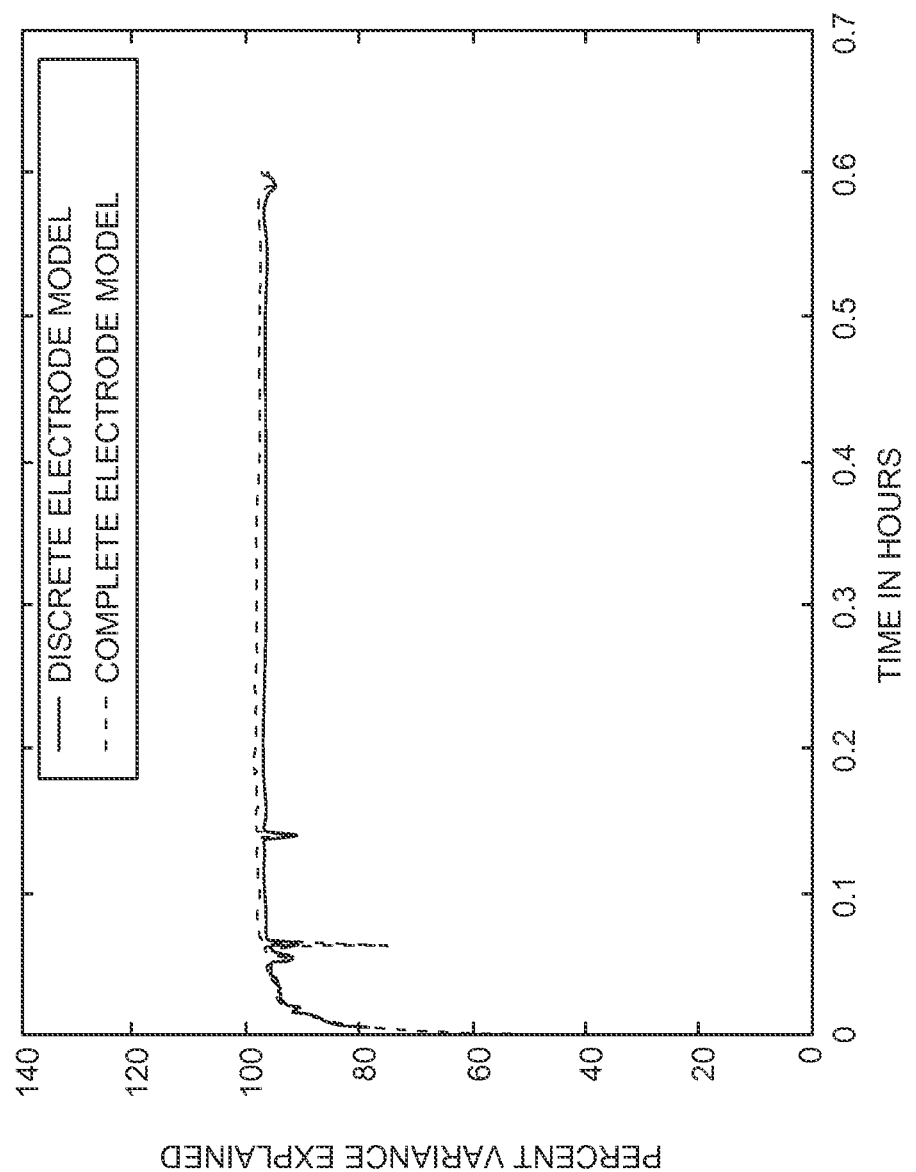
FIG. 5 compares a simplified discrete model and complete electrode model, in accordance with aspects of the present specification.
Figure 6:
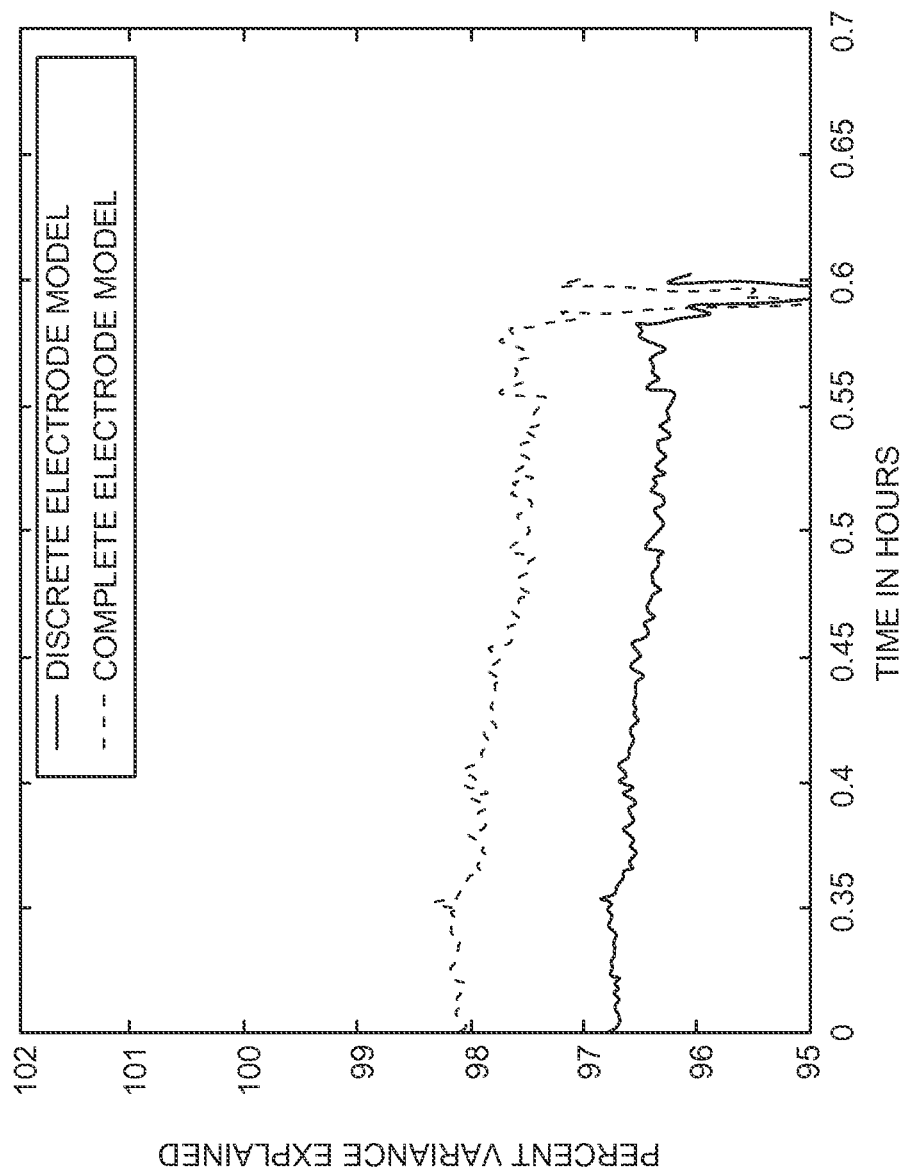
FIG. 6 further compares a simplified discrete model and complete electrode model, in accordance with aspects of the present specification.

With respect to the study results in the context of both the simplified discrete model described herein and the complete electrode model, the two models were compared with respect to their ability to explain changes in voltage in the data. With respect to this comparison, FIG. 5 depicts the percent of the variance explained for all time points and FIG. 6 depicts the asymptotic values of the percent variance explained for time points closer to the end of data collection. As shown, both models explain the preponderance of the variance of the data, though the complete electrode model performed slightly better with respect to this metric.

With this in mind, the compensated voltage measurements using the two models, or the voltage measurements that would have been seen if the changes at the electrode/skin interface had not occurred, were computed as follows:

$$y_{comp,D}(t) = y(t) - J_{z,D} \delta z^D(t) \quad (8)$$

$$y_{comp,CEM}(t) = y(t) - J_{z,CEM} \delta z^{CEM}(t) \quad (9)$$

where we compensate the measurements for changes in electrode contact impedances using either the discrete model (D) or the complete electrode model (CEM) and $J_{z,D}$ and $J_{z,CEM}$ are the Jacobian matrices for the measured voltages on the electrodes for the discrete model and the complete electrode model, respectively.

Figure 7:
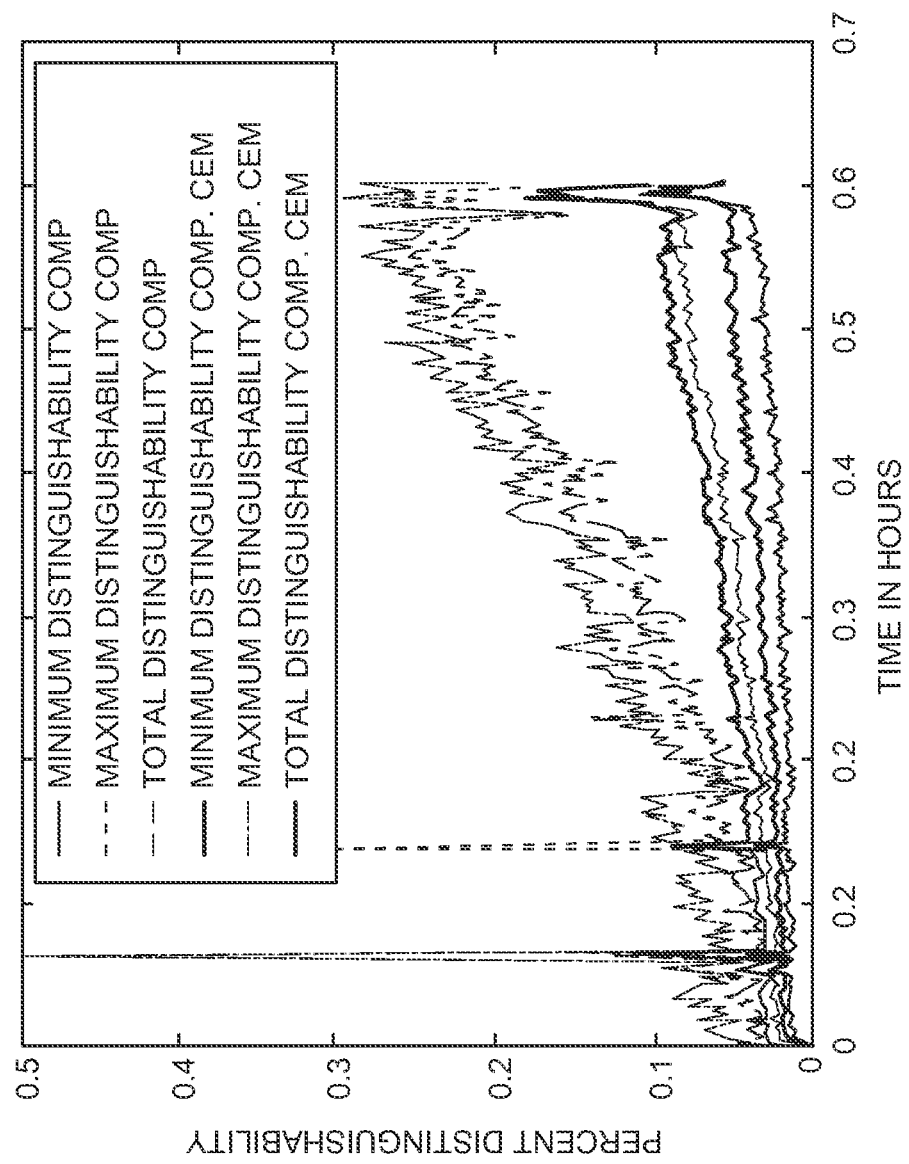
FIG. 7 depicts distinguishability over time using different compensated voltage models, in accordance with aspects of the present specification.

For the human subject data set, the distinguishabilities of the data compensated using the discrete simplified model and the complete electrode model were computed, with the results shown in FIG. 7. In general, it may be observed that the maximum distinguishability of the data compensated with the complete model is somewhat higher than that of the data compensated with the discrete model, indicating somewhat worse performance of the complete model given the assumption that large-scale global changes were not occurring in the brain of the subject during the experiment.

Simulation and experimental results—Electrical impedance measurement data was generated using a mesh derived from a segmented CT scan. The generated mesh included approximately 125,000 tetrahedral elements and was scaled such that the diameter of the head was approximately 20 cm. In the simulation, values of the dielectric properties of human tissue were used as shown in Table 1 for a modulation frequency of 10 kHz. The employed segmentation did not discriminate between white and gray matter, so all voxels labeled as "brain" tissue were assigned the mean of the white and gray matter admittivities at 10 kHz.

TABLE 1

| Tissue | Real Admittivity (S/m) | Imag. Admittivity (S/m) |
|---|---|---|
| Skin | 0.003 | 0.016 |
| Skull | 0.02 | 0.0003 |
| Brain | 0.0922 | 0.0097 |
| Blood | 0.7 | 0.0029 |

In the simulation, it was assumed that all of the above tissues were homogeneous and that, likewise, all electrodes were characterized by the same real contact impedance. One thousand realizations of the following four conditions were then simulated: (1) No change in conductivity in the head but added independent and identically distributed Gaussian noise to the measurements; (2) No change in conductivity in the head but added independent and identically distributed Gaussian noise to the measurements and independent and identically distributed electrode contact impedance changes with variances estimated from the human subject; (3) 5 ml bleed in the center of the head in addition to independent and identically distributed Gaussian noise added to the measurements; and (4) 5 ml bleed in the center of the head in addition to independent and identically distributed Gaussian noise and independent and identically distributed electrode contact impedance changes with variances estimated from the human subject experiment. For realizations (3) and (4), the simulation was performed by giving a set of voxels with a volume of 5 ml in the center of the head an admittivity equal to that of pure blood.

For each of these realizations, the log-likelihood of observing the measurements was computed given the assumption of a homogeneous, unchanging medium:

$$l_0 = (y - y_0)^H \Sigma_n^{-1} (y - y_0) \quad (10)$$

where $l_0$ is the log-likelihood of observing the measurements given the null hypothesis, the measurements are denoted by y, the measurements at time zero are given by the vector $y_0$, and $\Sigma_n$ is the noise covariance matrix, which is assumed to be known and diagonal. Note that $y^H$ represents the Hermitian transpose of the vector y. The compensated log-likelihood, where we have estimated the changes in electrode impedances that best explain the data, was also computed:

$$l_0^{comp} = (y_{comp} - y_0)^H \Sigma_n^{-1} (y_{comp} - y_0) \quad (11)$$

where $y_{comp}$ is estimated using equation (7).

Figure 8:
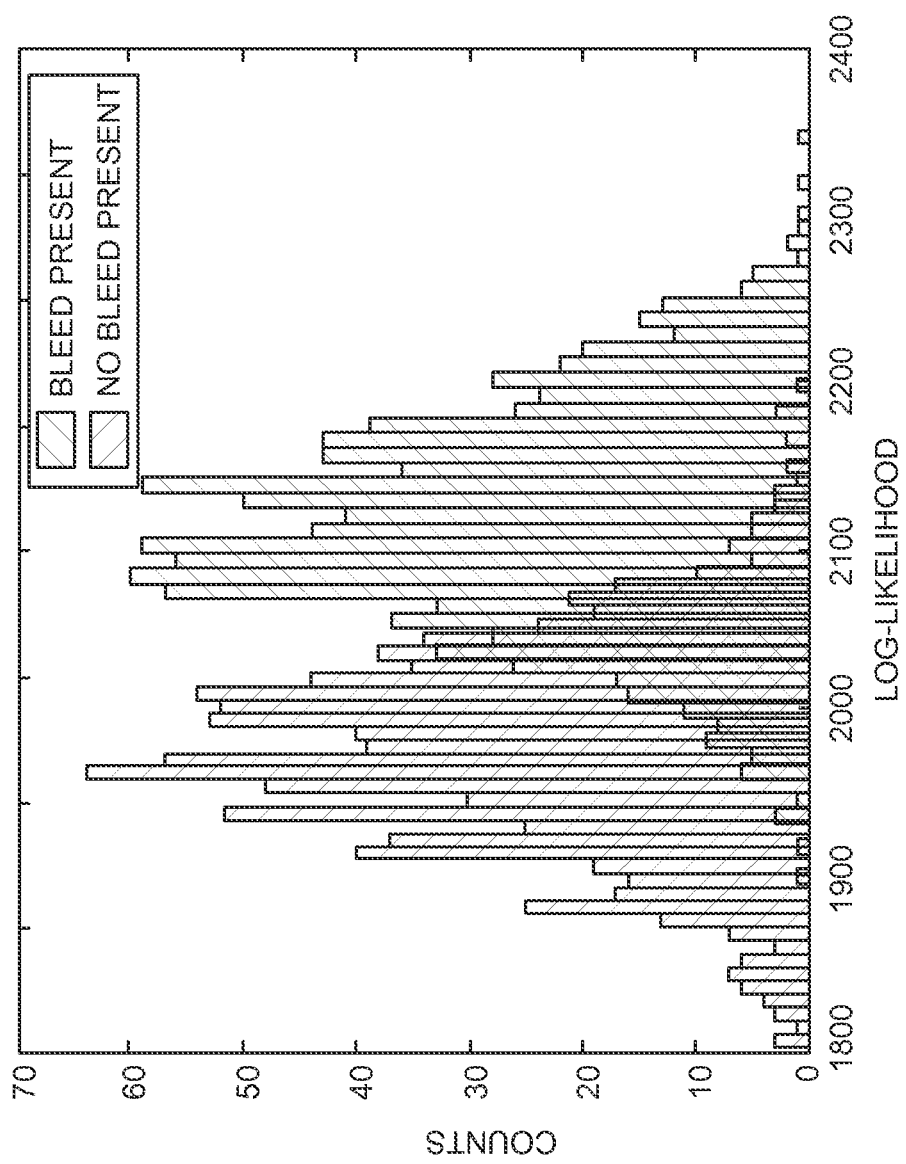
FIG. 8 depicts an example set of histograms for bleed and no bleed data, in accordance with aspects of the present specification.
Figure 9:
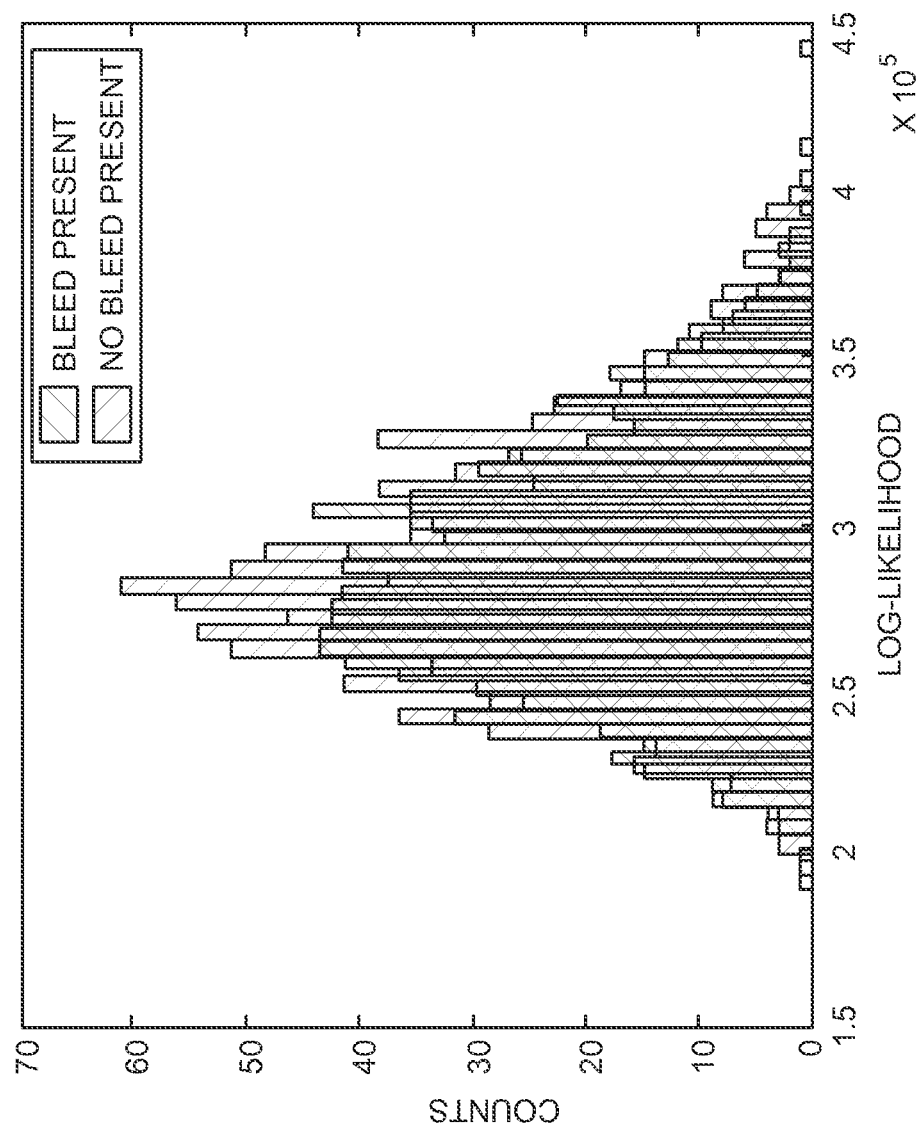
FIG. 9 depicts the histograms of FIG. 8 after addition of simulated electrode contact impedance changes, in accordance with aspects of the present specification.

The simulations were conducted for a maximum applied current of approximately 120 µA and over a range of noise levels. For each noise level, the Receiver Operating Characteristics (ROC) curve was computed for all possible values of the threshold in discriminating between the two classes. An example set of histograms (with the case of a bleed shown in the rightmost distribution and of no change shown in the leftmost distribution) for a noise standard deviation of 40 µV, is displayed in FIG. 8. As shown in FIG. 9, after large simulated electrode contact impedance changes were added to the data, the two histograms overlap almost completely. In particular, FIGS. 8 and 9, taken together, illustrate change detection performance with varying levels of independent, identically distributed (i.i.d.) Gaussian noise, with FIG. 8 illustrating a histogram of likelihood values for the two cases having a noise standard deviation of 40 µV (i.e., just noise, with invariant contact impedance) and FIG. 9 illustrating a histogram of likelihood values for the two cases having a noise standard deviation of 40 µV with the addition of added electrode contact impedance changes (i.e., noise plus varying contact impedance). Thus, FIGS. 8 and 9 illustrate, in the context of the "bleed" and "no bleed" simulation instances, respectively, a general distinguishability between instances when a bleed is present and when it is not which disappears once the realistic presence of contact impedance changes are added to the instances.

Figure 10:
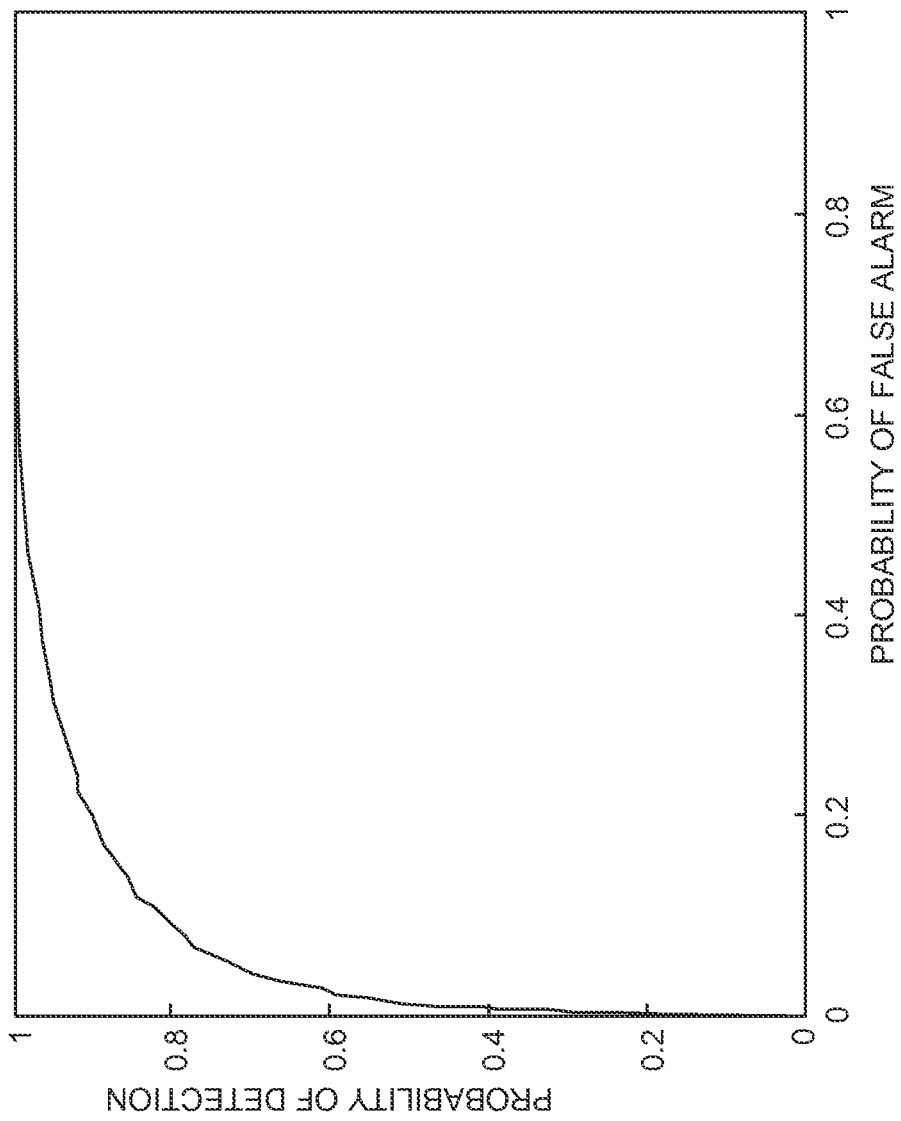
FIG. 10 depicts an ROC curve corresponding to the histograms of FIG. 8, in accordance with aspects of the present specification.

The detection performance of the system is quantified by examining the ROC curve, generated by computing the probability of detection and the probability of false alarm for each possible value of the log-likelihood threshold in discriminating between the "bleed" and "no bleed" cases. The ROC curve for a noise level of 40 µV where the electrode contact impedances do not vary, corresponding to the histogram displayed in FIG. 8, is shown in FIG. 10. An ideal ROC curve would have an area of 1.0 (i.e. a 100% probability of detection and a 0% probability of false alarm) and thus the area under the ROC curve (the AUC) is an objective metric for the detection performance of a system given a particular noise level, though other metrics are possible. For a noise level of 40 µV, the detection probability is maximized at 80% unless one was to increase the false-alarm probability to a level approaching 20%.

Figure 11:
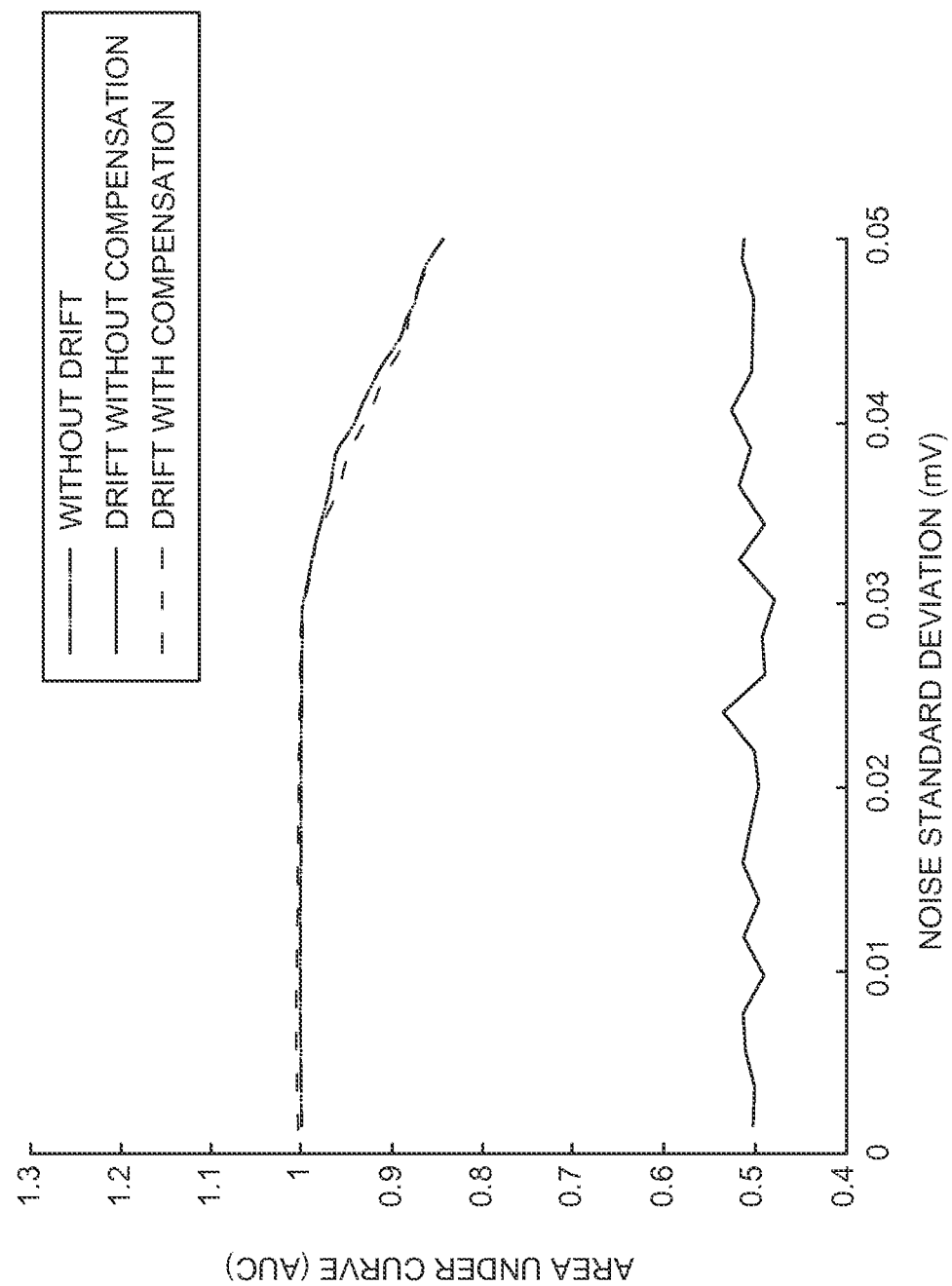
FIG. 11 depicts the area under the ROC curve for various noise levels with and without compensation for changes in electrode contact impedances, in accordance with aspects of the present specification.

The detection performance for certain of the cases described herein was empirically computed. In the case of no electrode contact impedance variations (i.e., FIG. 8), a gradual reduction in the area under the receiver operating characteristics curve (ROC) (i.e., the AUC), was observed as the noise level was increased. However, if there were electrode contact impedance variations typical of those seen in the human subject study (i.e., FIG. 9), a small bleed was not detectable at any noise level (i.e. the AUC was always approximately 0.5, or near random chance detectability.) Computing the compensated log-likelihood using Equation 11, first estimating the changes in electrode-skin contact impedances and removing their effect by compensation, there was only a very slight decrease in the achievable AUC for each noise level. A summary of these results is shown in FIG. 11, which shows that the achievable results with compensation as discussed herein are comparable to the absence of electrode drift altogether while the absence of compensation in the presence of electrode drift yields results comparable to random chance (i.e., 0.5) with respect to detection.

Figure 12:
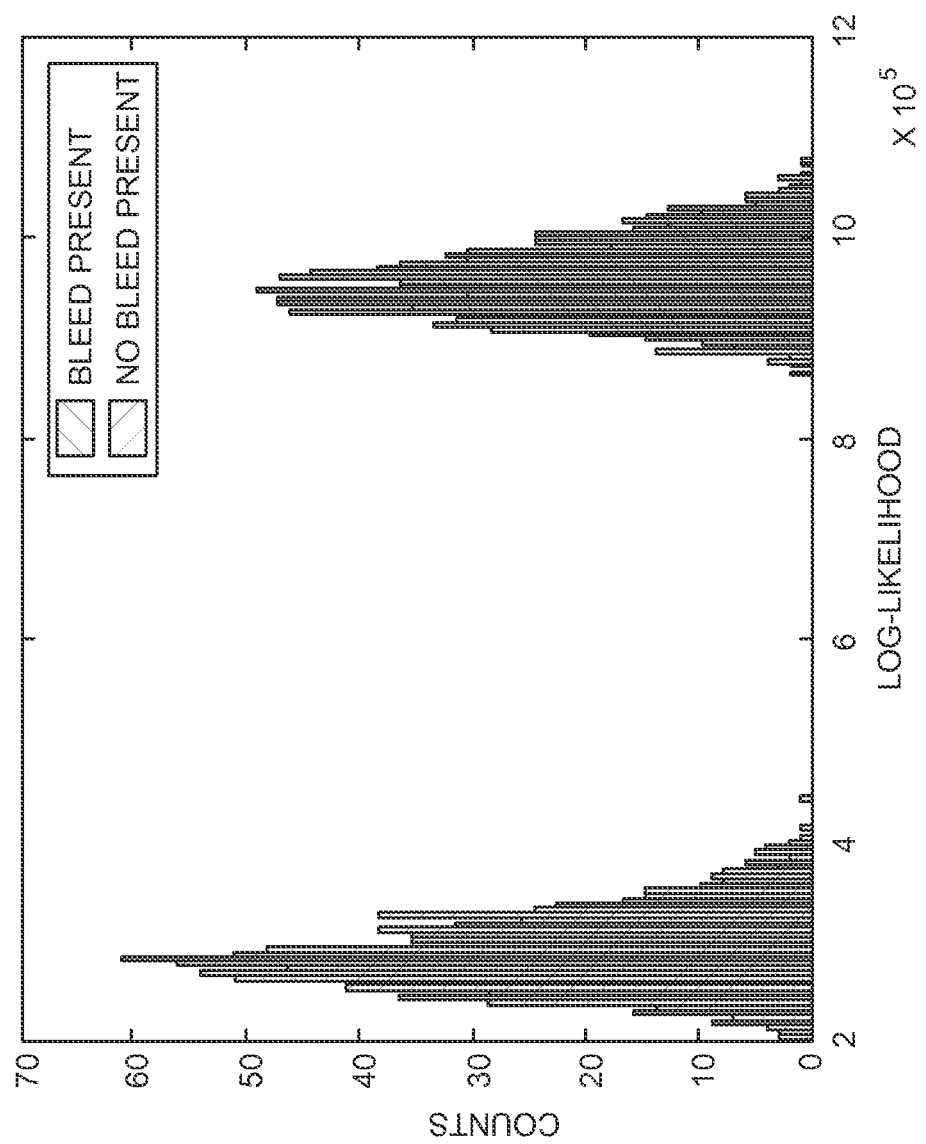
FIG. 12 depicts a set of histograms where no compensation for electrode contact impedance variations has been applied, in accordance with aspects of the present specification.

In addition, the case of a superficial bleed, rather than one located in the center of the brain, was considered. In particular, a 5 ml bleed was simulated very close to the electrode at the top of the head. As before, the cases of Gaussian independent, identically distributed noise only, added Gaussian noise with electrode contact impedance changes, and Gaussian identically distributed noise with electrode contact impedance changes and compensation of these changes algorithmically were simulated. The results in all cases were the same: an area under the curve of 1.0 for all simulated noise levels (0.002 mV to 0.05 mV.) A representative set of histograms is shown in FIG. 12, where no compensation for electrode contact impedance variations has been applied. These results indicate that the change in log-likelihood due to a small superficial bleed is much greater than that due to moderate electrode contact impedance variations. However, unlike the case of purely Gaussian noise with known variance, it is not known which threshold to choose a priori. The specific threshold is a function of the magnitude of the electrode contact impedance variations and for large variations, the two classes may no longer be separable.

Figure 13:
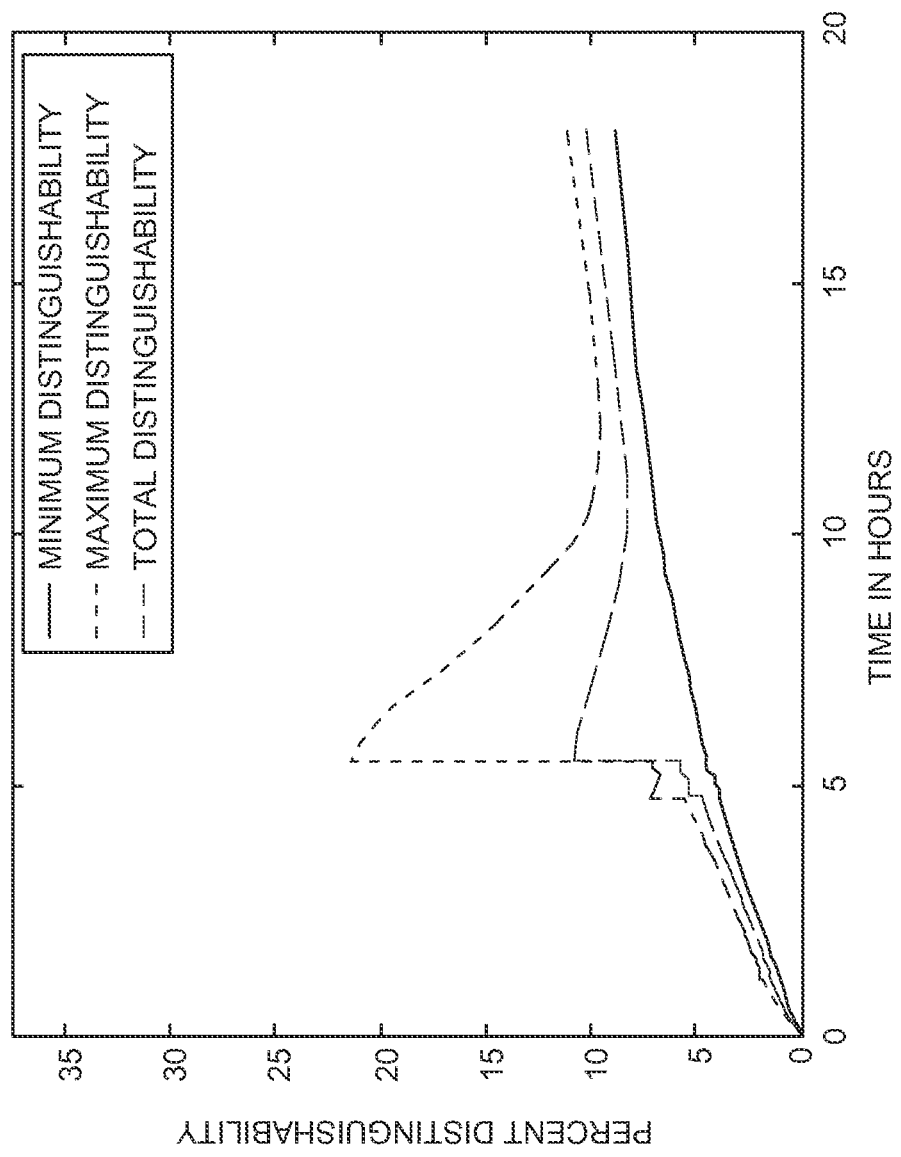
FIG. 13 depicts distinguishabilities without voltage compensation determined for a superficial bleed experiment, in accordance with aspects of the present specification.
Figure 14:
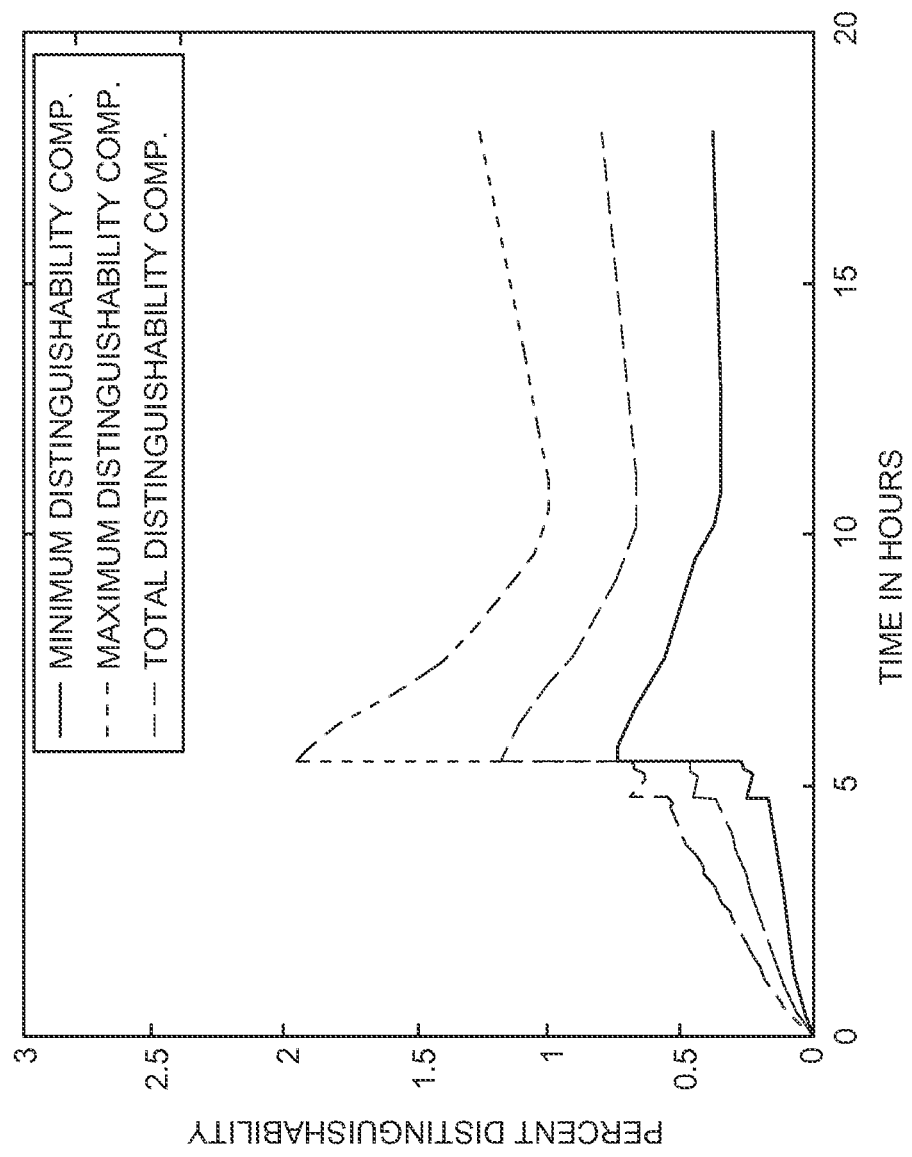
FIG. 14 depicts distinguishabilities with voltage compensation determined for a superficial bleed experiment, in accordance with aspects of the present specification.

In order to examine the detectability of a superficial bleed experimentally, a set of AgCl electrodes sewn into a stretchable mesh was placed onto a watermelon. After approximately 5 hours had passed, 3 ml of highly conductive electrode gel was injected near an electrode positioned approximately where the forehead would be on a human. The distinguishabilities of the electrode injection are shown in FIG. 13, without compensation for electrode contact impedance variations. The corresponding compensated distinguishabilities are shown in FIG. 14.

To a large extent, the increase in distinguishability due to electrode drift over time before and after the injection has been greatly reduced by compensation, although a residual component remains. The change in distinguishability due to the superficial injection is generally visible in both FIGS. 13 and 14 relative to the respective baseline distinguishabilities. However, the relative change in distinguishability is clearly present in all three change metrics (total, maximum and minimum distinguishability) in the compensated data (FIG. 14), whereas it is only present in two of the change metrics (total and maximum distinguishability) in the uncompensated data (FIG. 13). Thus, although compensation may reduce the baseline distinguishability, the ability to detect a change due to a variation in internal impedance is enhanced.

With the preceding simulation studies and experimental data in mind, the feasibility of detecting both superficial and deep bleeds in the brain with a volume as small as 5 ml with electrical impedance measurements and multi-electrode excitation patterns is shown. As noted, a number of algorithms may be employed for compensating for large changes at the electrode-skin interface that would tend to obscure the signal of interest.

Of particular note, a physiological state of interest or a change in such a state (such as internal bleeds, hydrocephalis, and so forth) can be detected using electrical impedance measurements without reconstruction of the electrical impedance measurements into an image (e.g., a tomographic image). Thus, detection of the physiological state or change in state can occur without implementing complex image reconstruction algorithms. In certain implementations, a metric (e.g., distinguishability, likelihood ratios, and so forth) may be computed and compared to reference metrics or thresholds, such as for changes over time or in comparison to a standard to determine the presence or absence of a physiological state of interest or of a change in such as state.

Technical effects of the invention include monitoring a state or change in state of a physiological parameter based on measured impedance data, where no images are reconstructed from the impedance data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for monitoring a physiological state of a patient, comprising:
    applying a pattern of electrical currents or voltages to the patient via a set of electrodes positioned on the patient;
    on one or more electrodes of the set of electrodes, measuring a resultant voltage or current in response to the applied pattern of electrical currents or voltages suitable for tomographic image reconstruction;
    calculating a change metric based upon the measured resultant voltage or current, wherein the change metric comprises one of a distinguishability metric or a likelihood ratio;
    determining the physiological state or a change in the physiological state of the patient based upon the change metric without reconstructing an image via the tomographic image reconstruction based on the measured resultant voltage or current, wherein determining the physiological state or the change in the physiological state comprises comparing the change metric to a reference metric, and based upon the comparison, providing a notification if the comparison indicates that an alarm condition or a diagnostic condition is met; and
    performing the tomographic image reconstruction based on the measured resultant voltage or current.

2. The method of claim 1, wherein the pattern of electrical currents or voltages is selected so as to optimize detection of the physiological state within the patient, the physiological state including a brain bleed.

3. The method of claim 2, comprising,
    after calculating the change metric based upon the measured resultant voltage or current, for one or more electrodes in the set of electrodes positioned on the patient, determining if an impedance that is estimated based on the measured resultant voltage or current has changed over time;
    for each electrode where it is determined that the estimated impedance has changed, calculating a compensated voltage or current to compensate for electrode-skin contact impedance variations at an electrode-skin interface based on an estimated change in contact impedances;
    based on the calculated compensated voltage or current for each electrode where it is determined that the estimated impedance has changed, modifying the pattern of electrical currents or voltages; and
    applying the modified pattern of electrical currents or voltages to the patient via the set of electrodes.

4. The method of claim 1, comprising,
    after calculating the change metric based upon the measured resultant voltage or current, for one or more electrodes in the set of electrodes positioned on the patient, determining if an impedance that is estimated based on the measured resultant voltage or current in response to the applied pattern of electrical currents or voltages suitable for tomographic image reconstruction has changed over time;
    for each electrode where it is determined that the estimated impedance has changed, calculating a compensated voltage or current; and
    calculating the change metric based at least in part on the compensated voltage or current for each electrode where it is determined that the estimated impedance has changed.

5. The method of claim 1, wherein the change metric further comprises a first measured data vector and the reference metric comprises a second measured data vector, wherein comparison of the change metric and the reference metric comprises computing a difference between the first measured data vector for the change metric and the second measured data vector for the reference metric, wherein the first and second measured data vectors are both derived from the patient but at different times, wherein the first measured data vector for the change metric comprises the measured resultant voltage or current from the one or more electrodes of the set of electrodes, and wherein the second measured data vector for the reference metric comprises a resultant voltage or current measured at an earlier time.

6. The method of claim 1, wherein the change metric further comprises a first measured data vector and the reference metric comprises a second measured data vector, wherein comparison of the change metric and the reference metric comprises computing a difference between the first measured data vector and the second measured data vector, wherein the first measured data vector is derived from the patient and the second measured data vector is derived from a population, wherein the first measured data vector for the change metric comprises the measured resultant voltage or current from the one or more electrodes of the set of electrodes, and wherein the second measured data vector for the reference metric comprises a resultant voltage or current measured at an earlier time.

7. The method of claim 6, wherein the change metric further includes a distance of the patient from a cluster within the population, including where the population includes a first set of patients with hemorrhagic strokes and a second set of patients with ischemic strokes each respectively clustered to generate reference metrics, the patient classified by his or her distance to each of the clusters via the monitored change metric with the respective stroke reference metrics.

8. The method of claim 1, wherein the pattern of electrical currents or voltages applied to the patient via the set of electrodes positioned on the patient is adaptively modified over time.

9. The method of claim 1, wherein the physiological state or the change in the physiological state comprises a change in a solid or liquid body tissue composition or a change in spatial distribution of the solid or liquid body tissue.

10. An electrical impedance physiological monitoring system, comprising:

a plurality of electrodes;
a plurality of electrical channels, wherein each electrode of the plurality of electrodes is in communication with one electrical channel of the plurality of electrical channels, the plurality of electrical channels comprising:
  at least one current source;
  at least one excitation source; and
  at least one response detector;
  wherein the at least one current source, the at least one excitation source, and the at least one response detector drive operation of one or more of the electrodes in communication with one of the electrical channels;
a processor-based monitor configured to operate the at least one excitation source and to receive signals from the at least one response detector in accordance with one or more processor-executable routines which, when executed on the processor-based monitor, cause acts to be performed comprising:
  operating the at least one excitation source to apply a pattern of electrical currents or voltages to a patient via the plurality of electrodes;
  operating the at least one response detector to measure a resultant voltage or current at the plurality of electrodes in response to the pattern of electrical currents or voltages suitable for tomographic image reconstruction;
  calculating a change metric based upon the operating the at least one response detector to measure the resultant voltage or current, wherein the change metric comprises one of a distinguishability metric or a likelihood ratio;
  determining a physiological state or a change in the physiological state of the patient based upon the change metric without reconstructing an image via the tomographic image reconstruction based on the measured resultant voltage or current, wherein determining the physiological state or the change in the physiological state comprises comparing the change metric to a reference metric, and based upon the comparison, providing a notification if the comparison indicates that an alarm condition or a diagnostic condition is met; and
  performing the tomographic image reconstruction based on the measured resultant voltage or current.

11. The electrical impedance physiological monitoring system of claim 10, wherein the at least one excitation source and the at least one response detector are integrated as a single component.

12. The electrical impedance physiological monitoring system of claim 10, wherein the processor-based monitor is further configured to execute one or more routines which, when executed, cause acts to be performed while determining the physiological state of the patient comprising:
  for the plurality of electrodes, determining if an impedance that is estimated based on the measured resultant voltage or current step has changed over time;
  for each electrode of the plurality of electrodes where it is determined that the estimated impedance has changed, calculating a compensated voltage;
  based on the calculated compensated voltage, modifying the pattern of electrical currents or voltages; and
  operating the at least one excitation source to apply the modified pattern of electrical currents or voltages to the patient via the plurality of electrodes.

13. The electrical impedance physiological monitoring system of claim 10, wherein the processor-based monitor is further configured to execute one or more routines which, when executed, cause acts to be performed while determining the physiological state of the patient comprising:
  for the plurality of electrodes, determining if an impedance that is estimated based on the measured resultant voltage or current step has changed over time;
  for each electrode of the plurality of electrodes where it is determined that the estimated impedance has changed, calculating a compensated voltage; and
  calculating the change metric based at least in part on the compensated voltage for each of the plurality of electrodes where it is determined that the estimated impedance has changed.

14. One or more non-transitory computer-readable media encoding one or more executable routines, wherein the one or more executable routines, when executed by a processor, cause the processor to:
  control an excitation source communicatively coupled to the processor to apply a pattern of electrical currents or voltages to a patient via a first set of electrodes positioned on the patient;
  control a response detector communicatively coupled to the processor to measure a resultant voltage or current via a second set of electrodes positioned on the patient in response to the applied pattern of electrical currents or voltages suitable for tomographic image reconstruction;
  calculate a change metric based upon the measured resultant voltage or current step, wherein the change metric comprises one of a distinguishability metric or a likelihood ratio;
  determine a physiological state or a change in the physiological state of the patient based upon the change metric without reconstructing an image via the tomographic image reconstruction based on the measured resultant voltage or current, wherein to determine the physiological state or the change in the physiological state step comprises comparing the change metric to a reference metric, and based upon the comparison, providing a notification if the comparison indicates that an alarm condition or a diagnostic condition is met; and
  perform the tomographic image reconstruction based on the measured resultant voltage or current.

15. The one or more non-transitory computer-readable media of claim 14, wherein the pattern of electrical currents or voltages is selected so as to optimize detection of the physiological state within the patient.

16. The one or more non-transitory computer-readable media of claim 14, wherein the one or more executable routines, when executed, further cause the processor to, while determining the physiological state of the patient:
  for one or more electrodes in the second set of electrodes, determine if an impedance that is estimated based on the measured resultant voltage or current step has changed over time;
  for each electrode in the second set of electrodes where it is determined that the impedance has changed, calculate a compensated voltage;
  based on the calculated compensated voltage, modify the pattern of electrical currents or voltages; and
  control the excitation source to apply the modified pattern of electrical currents or voltages to the patient via the first set of electrodes.

17. The one or more non-transitory computer-readable media of claim 14, wherein the one or more executable routines, when executed, further cause the processor to, while determining the physiological state of the patient:

- for one or more electrodes in the second set of electrodes, determine if an impedance that is estimated based on the measured resultant voltage or current step in response to the applied pattern of electrical currents or voltages suitable for tomographic image reconstruction has changed over time;
- for each electrode in the second set of electrodes where it is determined that the estimated impedance has changed, calculate a compensated voltage; and
- calculate the change metric based at least in part on the compensated voltage for each of the electrodes in the second set of electrodes where it is determined that the estimated impedance has changed.

* * * * *